(12) United States Patent
Schubart et al.

(10) Patent No.: US 6,849,409 B2
(45) Date of Patent: Feb. 1, 2005

(54) CELLULAR KINASES INVOLVED IN CYTOMEGALOVIRUS INFECTION AND THEIR INHIBITION

(75) Inventors: Daniel Schubart, Weil am Rhein (DE); Peter Habenberger, München (DE); Matthias Stein-Gerlach, München (DE); Dorian Bevec, Germering (DE)

(73) Assignee: Axxima Pharmaceuticals AG, Munich (DE)

( * ) Notice: Subject to any disclaimer, the term of this patent is extended or adjusted under 35 U.S.C. 154(b) by 0 days.

(21) Appl. No.: 09/981,397

(22) Filed: Oct. 16, 2001

(65) Prior Publication Data

US 2003/0082519 A1 May 1, 2003

Related U.S. Application Data

(60) Provisional application No. 60/240,750, filed on Oct. 16, 2000.

(51) Int. Cl.$^7$ ................................................ C12Q 1/68
(52) U.S. Cl. ..................... 435/6; 435/235.1; 435/325; 435/91.33
(58) Field of Search ..................... 435/6, 335.1, 325, 435/91.33; 530/350

(56) References Cited

U.S. PATENT DOCUMENTS

| | | | |
|---|---|---|---|
| 5,242,974 A | 9/1993 | Holmes | |
| 5,384,261 A | 1/1995 | Winkler et al. | |
| 5,405,783 A | 4/1995 | Pirrung et al. | |
| 5,412,087 A | 5/1995 | McGall et al. | |
| 5,424,186 A | 6/1995 | Fodor et al. | |
| 5,429,807 A | 7/1995 | Matson et al. | |
| 5,436,327 A | 7/1995 | Southern et al. | |
| 5,445,934 A | 8/1995 | Fodor et al. | |
| 5,472,672 A | 12/1995 | Brennan | |
| 5,527,681 A | 6/1996 | Holmes | |
| 5,529,756 A | 6/1996 | Brennan | |
| 5,545,531 A | 8/1996 | Rava et al. | |
| 5,554,501 A | 9/1996 | Coassin et al. | |
| 5,556,752 A | 9/1996 | Lockhart et al. | |
| 5,561,071 A | 10/1996 | Hollenberg et al. | |
| 5,599,895 A | 2/1997 | Heider | |
| 5,624,711 A | 4/1997 | Sundberg et al. | |
| 5,639,603 A | 6/1997 | Dower et al. | |
| 5,658,734 A | 8/1997 | Brock et al. | |
| 5,807,522 A | 9/1998 | Brown et al. | |
| 6,087,102 A | 7/2000 | Chenchik et al. | |
| 6,211,337 B1 * | 4/2001 | Baichwal et al. | 530/350 |

FOREIGN PATENT DOCUMENTS

| | | |
|---|---|---|
| EP | 742 287 | 11/1996 |
| EP | 799 897 | 10/1997 |
| JP | 9183764 A | 7/1997 |
| JP | 11124368 A | 5/1999 |
| JP | 11189529 A | 7/1999 |
| WO | WO 93/17126 | 9/1993 |
| WO | WO 95/11995 | 5/1995 |
| WO | WO 95/35505 | 12/1995 |
| WO | WO 97/02039 | 1/1997 |
| WO | WO 98/48836 | 11/1998 |
| WO | WO 99/32463 | 6/1999 |
| WO | WO 99/55335 | 11/1999 |
| WO | WO 99/65513 | 12/1999 |
| WO | WO 00/011218 A1 * | 3/2000 |

OTHER PUBLICATIONS

Zhu et al, PNAS USA, 1998, vol. 95, pp. 14470–14475.*
Bell et al., *British J. Cancer*, 77:1852–1856 (1998).
Bhagwat et al., *DDT*, 4:472–479 (1999).
Blank et al., *J. Biol. Chem.*, 27:5361–5368 (1996).
Goekjian, et al., *Curr. Med. Chem.*, 6:877–903 (1999).
Goldenberg, *Clinical Therapeutics*, 21:309–318 (1999).
Hughes et al., *Proc. Natl. Acad. Sci*, 87:6728–7–6732 (1990).
Keates et al., *J. Immunol.*, 163:5552–5559 (1999).
Kuroyanagi et al., *Biochem. Biophys. Res. Commun.*, 242:357–364 (1998).
Marshall, *Science*, 286:444–447 (1999).
Mitamura et al., *J. Biol. Chem.*, 270:1015–1019 (1995).
Naumann et al., *J. Biol. Chem.*, 274:31655–31662 (1999).
Prenzel et al., *Nature*, 402:884–888 (1999).
Raingeaud et al., *Mol. Cell. Biol.*, 16:1247–1255 (1996).
Revel et al., *Drugs of the Future*, 23:751–766 (1998).
Service, *Science*, 289:1673.
Tarnawski et al., *J. Clin. Gastroenterol.*, 27(Suppl. 1):S12–S20 (1998).
Traxler et al., *Drugs of the Future*, 20:1281–1274 (1995).
Wang et al., *J. Cell. Biol.*, 140:737–750 (1998).
Wang et al., *Genomics*, 57:310–315 (1999).
Wojtowitz–Praga et al., *Investig. New Drugs*, 15:61–75 (1997).
Wysk et al., *PNAS USA*, 96:3763–3768 (1999).

* cited by examiner

*Primary Examiner*—Ali R. Salimi
(74) *Attorney, Agent, or Firm*—Leon R. Yankwich; Michael R. Wesolowski

(57) ABSTRACT

The role of certain cellular kinases active during Human Cytomegalovirus infection is disclosed. These cellular kinases are useful to detect HCMV infection, and can be used to screen for cellular kinase inhibitors. Cellular kinases inhibitors, which effectively downregulate these key cellular components, serve as effective therapeutics against HCMV infection.

1 Claim, 2 Drawing Sheets

CELLULAR KINASES INVOLVED IN CYTOMEGALOVIRUS INFECTION AND THEIR INHIBITION

CROSS REFERENCE TO RELATED APPLICATIONS

This application claims priority to U.S. provisional application Ser. No. 60/240,750, filed Oct. 16, 2000.

The present invention is in the fields of molecular biology and virology. The present invention is directed to novel methods for treating Cytomegalovirus using kinase inhibitors.

BACKGROUND OF THE INVENTION

Human Cytomegalovirus (HCMV) is a highly specific β-herpesvirus. Primary infection of healthy children and adults is usually asymptomatic, with a minority of cases developing a mononucleose-like syndrome. In contrast, congenital infection (U.S. 0.2%–2.2% per live birth; aprox. 40,000 per year) leads to several neurological defects in 10–15% of infected neonates. Immunocompromised patients represent another host group facing serious disease complications caused by HCMV infection or reactivation of a persistent infection. Up to 40% of the AIDS patients, for example, develop retinitis, pneumonitis, gastroenteritis or disseminated HCMV disease. In addition, allograft recipients (20,000 allograft transplantations per year in the U.S.) are often infected (or superinfected) by virus from the transplanted organ.

Clinical symptoms in the posttransplant period include prolonged fever, leukopenia, thrombocytopenia, atypical lymphocytosis, elevated hepatic transaminases and decreased graft survival. In bone marrow transplantations, HCMV infection is associated with high mortality rates (80–90% for untreated HCMV pneumonia).

Current approaches to develop therapeutics against Cytomegalovirus (CMV) have focused on antiviral agents per se; for example viral polymerase inhibitors. In fact, high mortality rates have been dramatically reduced by new antiviral agents. Current CMV therapeutics possess severe drawbacks, however. For example, Fomivirsen (Vitravene, formerly ISIS 2922) is typically administered by injection directly into the eye every 2 or 4 weeks. Ganciclovir is available for intravenous (Cytovene) or oral administration, and as an implant in the case of retinitis; unfortunately, toxic complications including leukopenia and thrombocytopenia frequently develop. Foscarnet (Foscavir; phosphonoformic acid), another antiviral agent, exhibits considerable renal toxicities and is only available in intravenous form (which is also true for Cidofovir (Vistide), another CMV therapeutic). In addition, CMV replication resumes soon after Ganciclovir and Foscarnet treatment is halted. Finally, Ganciclovir- and Foscarnet-resistant strains of CMV are emerging.

Although treatment of HCMV-induced disease has been improved with these inhibitors of the viral polymerase and preemptive or early antiviral therapy in transplant patients, there is a need in the art for a new class of HCMV therapeutics with better oral bioavailability and reduced toxic effects. This is especially true in the treatment of retinitis in AIDS patients, where CMV infection must be controlled for long periods of time.

Recent research has revealed how cells communicate with each other to coordinate the growth and maintenance of the multitude of tissues within the human body. A key element of this communication network is the transmission of a signal from the exterior of a cell to its nucleus, which results in the activation or suppression of specific genes. This process is called signal transduction.

An integral part of signal transduction is the interaction of cytokines, their receptors, and intracellular signal transduction molecules. Cytokines serve as messengers that bind to receptors on the surface of a target cell. As a result of the binding, the receptors activate a cascade of downstream signaling molecules, thereby transmitting the message from the exterior of the cell to its nucleus. Signal transduction to the nucleus modulates specific gene expression (i.e., transcription and translation), which results in either the upregulation or downregulation of specific proteins that carry out a particular biological function.

Viral infection disrupts normal signal transduction, which leads to cellular malfunctioning resulting in a disease state. Specifically, interference of HCMV with relevant human primary cells is necessary for the virus to create an environment that allows it to grow and replicate, and in turn cause disease in the infected individual. Current research efforts have failed to elucidate all the specific intracellular signal pathways affected by HCMV infection, however. Discovery of the signal transduction pathways and specific intracellular signal transduction molecules affected by CMV infection would represent a tremendous advance in the understanding of the induction and progression of CMV infection processes and provide new avenues for the development of a novel class of effective therapeutics for the treatment of CMV.

Thus, object of the present invention is to provide methods for detecting, preventing and/or treating Cytomegalovirus infection and/or associated diseases, methods for the identification of compounds useful for preventing and/or treating Cytomegalovirus infection and/or associated diseases and for regulating the production of Cytomegaloviruses.

The object of the present invention is solved by the teaching of the independent claims. Further advantageous features, aspects and details of the invention are evident from the dependent claims, the description, and the examples of the present application.

DESCRIPTION OF THE INVENTION

The present invention is based upon the finding of a group of cellular kinases that are specifically upregulated as a result of CMV infection. The antiviral therapeutic research approach described herein, focuses on discovering the cellular signal transduction pathways involved in viral infection. Identification of the cellular signal transduction molecules, key to viral infection provides for, among other things, novel diagnostic methods, especially assays, and compositions useful therefore, novel targets for antiviral therapeutics, a novel class of antiviral therapeutics, and new screening assays and materials to discover new antiviral agents.

This approach led to the development of a novel microarray platform technology, wherein a microarray of more than 1100 signal transduction cDNAs was developed. This unique microarray technology was used to identify RNA expression patterns (e.g., upregulation or downregulation) unique to CMV infected host cells. Differential display techniques were used to pinpoint those signal transduction molecules useful as targets for drug intervention. Effective manipulation of these virally-controlled intracellular signal transduction pathways can alter (slow or stop altogether) the course of viral growth.

It is now revealed for the first time that the cellular protein kinases RICK (also known as CARDIAK; RIP2), RIP, NIK (also known as HGK; MAP4K4), MKK3 (also known as MEK3), and SRPK-2 are specifically and uniquely upregulated in a cell as a result of CMV infection. These cellular kinases therefore identify novel diagnostic and therapeutic targets for CMV infection.

Surprisingly, it was found that the following human cellular targets are significantly upregulated compared with uninfected human foreskin fibroblasts cells:

| target | upregulation |
|--------|--------------|
| RICK   | 3.6 fold     |
| RIP    | 2.6 fold     |
| NIK    | 4.0 fold     |
| MKK3   | 2.5 fold     |
| SRPK-2 | 2.2 fold     |

Based upon the research work reported herein, one aspect of the present invention is directed to a method, preferably a screening assay, for identifying compounds useful for treating and/or preventing Cytomegalovirus infection and/or diseases associated therewith. Specifically, this assay involves contacting a test compound with one or more cellular kinases selected from the group consisting of RICK, RIP, NIK, MKK3, and SRPK-2, and detecting a change, normally a decrease, in activity of said cellular kinase. This method was used for the identification of the RICK and RIP inhibitors shown below in Table 1 and Table 2.

Another aspect of the invention is directed to a diagnostic method for detecting Cytomegalovirus infection and/or associated diseases in an individual or in cells and/or in cell lysates. This assay involves providing a sample from the individual or providing a sample from said cells, respectively, and detecting activity of one or more cellular kinases selected from the group consisting of RICK, RIP, NIK, MKK3, and SRPK-2. The term "individual" preferably refers to mammals, especially humans or ruminants.

Also described in the present invention are monoclonal or polyclonal antibodies which bind to a cellular kinase selected from the group consisting of RICK, RIP, NIK, MKK3, and SRPK-2.

A further aspect of the present invention relates to a method for preventing and/or treating Cytomegalovirus infection and/or associated diseases in an individual by administering a pharmaceutically effective amount of an inhibitor to said individual, wherein said inhibitor inhibits at least partially the activity of one or more cellular kinases selected from the group consisting of RICK, RIP, NIK, MKK3, and SRPK-2, or wherein said inhibitor inhibits at least partially the production of one or more cellular kinases selected from the group consisting of RICK, RIP, NIK, MKK3, and SRPK-2.

As used herein, the term "inhibitor" refers to any compound capable of downregulating, decreasing, reducing, suppressing or inactivating the amount and/or activity of at least one human cellular protein kinase selected from the group consisting of RICK, RIP, NIK, MKK3, and SRPK-2. Generally, said inhibitors, including suicide inhibitors, may be proteins, oligo- and polypeptides, nucleic acids, genes, small chemical molecules, or other chemical moieties. Suitable inhibitors are monoclonal or polyclonal antibodies which bind to at least one cellular kinase selected from the group consisting of RICK, RIP, NIK, MKK3, and SRPK-2.

Based on the surprising results reported herein, one aspect of the present invention is directed to a method for regulating the production of Cytomegalovirus in an individual by administering an individual a pharmaceutically effective amount of an inhibitor wherein said inhibitor inhibits at least partially the activity of one or more cellular kinases selected from the group consisting of RICK, RIP, NIK, MKK3, and SRPK-2, or wherein said inhibitor at least partially inhibits the production of one or more cellular kinases selected from the group consisting of RICK, RIP, NIK, MKK3, and SRPK-2.

A similar aspect relates to a method for regulating the production of Cytomegalovirus in cells by administering the cells a pharmaceutically effective amount of an inhibitor wherein said inhibitor inhibits at least partially the activity of one or more cellular kinases selected from the group consisting of RICK, RIP, NIK, MKK3, and SRPK-2, or wherein said inhibitor at least partially inhibits the production of one or more cellular kinases selected from the group consisting of RICK, RIP, NIK, MKK3, and SRPK-2 in the cells.

Yet another aspect of the invention is directed to a method for regulating the expression of at least one cellular kinase selected from the group consisting of RICK, RIP, NIK, MKK3, and SRPK-2 in an individual comprising the step of administering the individual a pharmaceutically effective amount of an inhibitor wherein said inhibitor inhibits at least partially the transcription of DNA or the translation of RNA encoding one of said cellular kinases.

A further aspect relates to a method for regulating the expression of at least one cellular kinase selected from the group consisting of RICK, RIP, NIK, MKK3, and SRPK-2 in the cells comprising the step of administering the cells a pharmaceutically effective amount of an inhibitor wherein said inhibitor inhibits at least partially the transcription of DNA or the translation of RNA encoding one of said cellular kinases.

As used herein, the term "regulating expression and/or activity" generally refers to any process that functions to control or modulate the quantity or activity (functionality) of a cellular component. Static regulation maintains expression and/or activity at some given level. Upregulation refers to a relative increase in expression and/or activity. Accordingly downregulation refers to a relative decrease in expression and/or activity. In the present invention, regulation is preferably the downregulation of a cellular component. Downregulation is synonymous with inhibition of a given cellular component's activity.

Beside inhibitors also activators may be useful for treating Cytomegalovirus infection by increasing the activity of at least one of the cellular protein kinases RICK, RIP, NIK, MKK3, and SRPK-2. Thus, a method for preventing and/or treating Cytomegalovirus infection and/or associated diseases in an individual is disclosed. Said method comprises administering a pharmaceutically effective amount of an activator to an individual, wherein said activator activates at least partially the activity of one or more cellular kinases selected from the group consisting of RICK, RIP, NIK, MKK3, and SRPK-2, or wherein said activator activates or stimulates at least partially the production of one or more cellular kinases selected from the group consisting of RICK, RIP, NIK, MKK3, and SRPK-2.

Furthermore, a method for regulating the production of Cytomegalovirus either in cells or in an individual is described. Said methods comprise administering an individual or to cells a pharmaceutically effective amount of an activator wherein said activator activates at least partially the activity of one or more cellular kinases selected from the group consisting of RICK, RIP, NIK, MKK3, and SRPK-2, or wherein said activator at least partially activates or stimulates the production of one or more cellular kinases selected from the group consisting of RICK, RIP, NIK, MKK3, and SRPK-2.

As used herein, the term "activator" refers to any chemical compound which is able to upregulate, increase, activate, or stimulate the activity of at least one human cellular protein kinase selected from the group consisting of RICK, RIP, NIK, MKK3, and SRPK-2 or which is able to upregulate, increase, activate, or stimulate the expression of at least one of said cellular kinases. Activators comprise proteins, oligo- and polypeptides, nucleic acids, genes, and preferably small chemical molecules, or other chemical moieties.

Still another aspect of the present invention is directed to either a method for regulating the expression of at least one cellular kinase selected from the group consisting of RICK, RIP, NIK, MKK3, and SRPK-2 in an individual or for regulating the expression of at least one of said kinases in cells. These methods comprise the step of administering the individual or the cells a pharmaceutically effective amount of an activator wherein said activator activates at least partially the transcription of DNA or the translation of RNA encoding one of said cellular kinases.

Furthermore, oligonucleotides are disclosed which bind to the DNA or RNA encoding a cellular kinase selected from the group consisting of RICK, RIP, NIK, MKK3, and SRPK-2. Said oligonucleotides can be used as suitable inhibitors within the aforementioned methods.

Some methods of the present invention identify compounds useful for prophylaxis and/or treatment of Cytomegalovirus infection and/or associated disease by screening a test compound, or a library of test compounds, for its ability to inhibit at least one of the above-mentioned human cellular protein kinases identified herein as characteristically upregulated during HCMV replication. Using this method the compounds A to E have been identified as RICK inhibitors and the compounds F to H have been identified as RIP inhibitors. Thus, the use of these compounds as inhibitors of RICK or RIP is disclosed. Furthermore, these compounds can be used for manufacturing a pharmaceutical composition for prophylaxis and/or treatment of Cytomegalovirus infection and/or diseases associated with Cytomegalovirus infection.

A variety of assay protocols and detection techniques are well known in the art and easily adapted for this purpose by a skilled practitioner. Such methods include, but are not limited to, high throughput assays (e.g., microarray technology, phage display technology), and in vitro and in vivo cellular and tissue assays.

Thus, some embodiments of the present invention may comprise a solid support useful for detecting Cytomegalovirus infection in a cell or an individual. Preferably the solid support comprises immobilized oligonucleotides, wherein the oligonucleotides are capable of detecting activity of one or more cellular kinases selected from the group consisting of: RICK, RIP, NIK, MKK3, and SRPK-2.

Another aspect of the invention includes a solid support useful for screening compounds useful for treating Cytomegalovirus. Preferred embodiments include a solid support comprising one or more immobilized oligonucleotides, wherein the oligonucleotide(s) encode one or more cellular kinases selected from the group consisting of RICK, RIP, NIK, MKK3, and SRPK-2. In another preferred embodiment, the solid support comprises one or more immobilized cellular kinases selected from the group consisting of: RICK, RIP, NIK, MKK3, and SRPK-2.

Accordingly, another aspect of the present invention is directed to a novel therapeutic composition useful to treat an individual afflicted with Cytomegalovirus comprising one or more inhibitors capable of inhibiting activity of one or more of the cellular kinases selected from the group consisting of RICK, RIP, NIK, MKK3, and SRPK-2. In addition thereto, a novel pharmaceutical composition could comprise at least one inhibitor capable of regulating the production of HCMV by inhibiting the expression of at least one cellular kinase selected from the group consisting of RICK, RIP, NIK, MKK3, and SRPK-2.

Another group of suitable therapeutic compositions useful for prophylaxis and/or treatment of CMV comprises at least one activator which is able to increase the activity of one or more cellular kinases selected from the group consisting of RICK, RIP, NIK, MKK3, and SRPK-2 or which is capable of increasing the expression of at least one cellular kinase selected from the group consisting of RICK, RIP, NIK, MKK3, and SRPK-2.

Said pharmaceutical compositions may further comprise pharmaceutically acceptable carriers, excipient, diluents, fillers, binders, disintegrants, lubricants, glidents, coloring agents, flavoring agents, opaquing agents, and/or plasticizers.

DETAILED DESCRIPTION OF THE INVENTION

Figure 1:
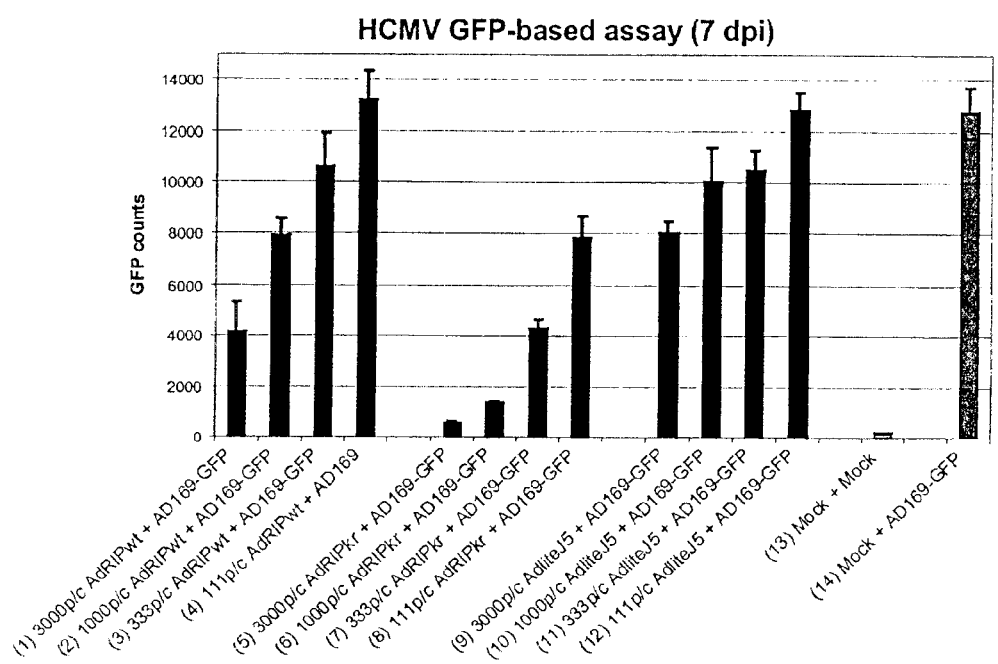
FIG. 1 is a bar graph showing the reduction rates in HCMV replication of HHF cells pre-infected with Adenovirus containing the RIP wildtype sequence (AdRIPwt; 1–4) and a RIP inactive mutant (AdRIPkr; 5–8).

Utilizing microarray technology, a unique microarray of more than 1100 signal transduction cDNAs was developed. This array was used to compare signal transduction mRNA expression patterns (e.g., upregulation or downregulation) in primary human cells before and after infection with HCMV at various timepoints of infection. Interference of the HCMV with the cellular signaling events is reflected in differential gene expression when compared to the uninfected cellular signaling. Results from this novel signal transduction microarray analysis revealed significant upregulation of cellular protein kinases RICK, RIP, NIK, MKK3, and SRPK-2, as unique to CMV infected host cells. These findings were confirmed utilizing conventional Northern and Western blot analyses.

Disclosed herein is the first report describing the role of cellular kinases; RICK, RIP, NIK, MKK3, and SRPK-2 in the signal transduction of CMV viral infection process. As a result of these discoveries, a novel class of compounds, i.e., RICK, RIP, NIK, MKK3, and SRPK-2 inhibitors, are identified as useful for altering the course of CMV infection.

To perform initial tests for compounds that inhibit RICK activity in a cellular assay, RICK was transiently overexpressed in HEK-293 cells, immunoprecipitated and incubated with different concentrations of test compounds before in-vitro kinase assays were performed (Example 10). According to the method for identifying compounds useful for inhibiting the cellular kinase RICK and therefore useful for treating and/or preventing Cytomegalovirus infection and/or diseases associated with Cytomegalovirus infection, a test compound is contacted with the cellular kinase RICK according to the RICK assay protocol disclosed in example 10. The test compound dissolved in DMSO is added to the RICK assay solution at concentrations between 100 nM and 50 μM. Thereafter, radioactively labeled ATP is added and kinase activity of RICK is determined by detecting the autophosphorylation of RICK via radioactivity measurement. The five compounds listed in the following Table 1 were identified using said method. These compounds showed inhibition of RICK kinase activity with an $IC_{50}$ between about 100 nM and 1 μM and an inhibition of HCMV with an $IC_{50}$ between about 1 and 8 μM, respectively. The $IC_{50}$ values of HCMV inhibition were obtained by the use of at least one assay protocol selected from a) virus replication assay, b) plaque assay, c) GFP (Green Fluorescent Protein) infection assay, and d) indirect immunofluorescence analysis as disclosed in example 12. Thus, the five compounds A to E mentioned below and/or pharmaceutically acceptable salts thereof can be used as inhibitors of the cellular protein kinase RICK and as pharmaceutically active compounds for the treatment and/or prophylaxis of HCMV infection. Furthermore, these compounds are suitable for the manufacture of a pharmaceutical composition for prophylaxis and/or treatment of Cytomegalovirus infection and/or diseases associated therewith.

TABLE 1

Inhibitors of RICK and HCMV

| compound | structure | $IC_{50}$ RICK | $IC_{50}$ HCMV |
|---|---|---|---|
| A<br>AX6548 | 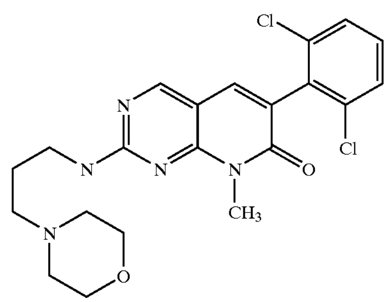 | 1 μM | 6.8 μM |
| B<br>AX6558 | 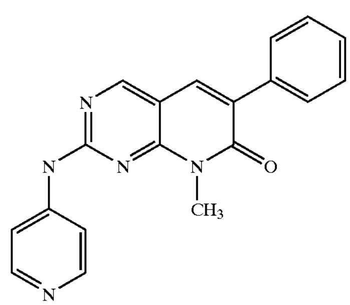 | 500 nM | 1.4 μM |
| C<br>AX6549 | 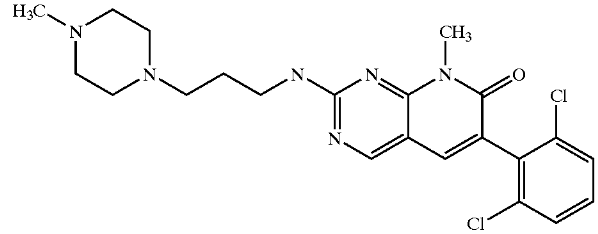 | 1 μM | 6.2 μM |

TABLE 1-continued

Inhibitors of RICK and HCMV

| compound | structure | IC$_{50}$ RICK | IC$_{50}$ HCMV |
|---|---|---|---|
| D AX5828 | (structure of 6,7-diethoxyquinazoline with 3-bromophenylamine at position 4) | 500 nM | 7.6 μM |
| E AX3359 | (structure of 6,7-dimethoxyquinazoline with 3-bromophenylamine at position 4) | 500 nM | 5.7 μM |

The compounds A to E have the following names:
Compound A: 6-(2,6-Dichlorophenyl)-8-methyl-2-(3-morpholin-4-yl-propylamino)-8H-pyrido[2,3-d]pyrimidin-7-one;
Compound B: 8-methyl-6-phenyl-2-(pyridin-4-yl-amino)-8H-pyrido[2,3-d]pyrimidin-7-one;
Compound C: 6-(2,6-Dichlorophenyl)-8-methyl-2-[3-(4-methylpiperazin-1-yl)-propylamino]-8H-pyrido[2,3-d]pyrimidin-7-one;
Compound D: (3-Bromophenyl)-(6,7-diethoxyquinazolin-4-yl)-amine;
Compound E: (3-Bromophenyl)-(6,7-dimethoxyquinazolin-4-yl)-amine.

From the results observed with the compounds shown in Table 1 it is proved that RICK is an important target for the treatment of HCMV and diseases associated with HCMV infection. Inhibitors of the human cellular protein kinase RICK may serve as new pharmaceutical substances for prophylaxis and/or treatment of Cytomegalovirus infection and/or diseases associated with CMV infection.

In addition to the chemical validation of RICK described above, a genetic validation of RICK in HCMV infection was performed. Wildtype and mutated RICK was expressed in HFF cells with a modified Adenovirus as vehicle (Example 9). The expression of both, wildtype and mutated RICK, caused a dramatic reduction in HCMV replication (cf. FIG. 2). Also these data confirm RICK as a valuable therapeutic target in HCMV treatment. As known in the art and as used herein, "RICK" refers to a protein kinase also known as "CARDIAK" and as "RIP2", is a RIP-like kinase. RICK is essentially characterized as comprising an N-terminal serine-threonine kinase catalytic domain and a C-terminal region containing a caspase-recruitment domain (referred to as "CARD").

To perform initial tests for compounds that inhibit RIP activity in a cellular assay, RIP was transiently overexpressed in HEK-293 cells, immunoprecipitated and incubated with different concentrations of test compounds before in-vitro kinase assays were performed (Example 11). In order to identify compounds suitable for inhibiting the cellular kinase RIP and, thus, suitable for treating and/or preventing Cytomegalovirus infection and/or diseases associated with Cytomegalovirus infection the inventive method according to claim 1 was used. A test compound was contacted with the cellular kinase RIP according to the RIP assay protocoll disclosed in example 11. The test compound dissolved in DMSO is added to the RIP assay solution at concentrations between 100 nM and 50 μM. Radioactively labeled ATP was used as co-substrate of RIP and autophosphorylation was detected via measurement of incorporation of radioactivity into the RIP protein. Thereafter, phosphorylation rates with and without test compounds were compared. The three compounds listed in the following Table 2 showed inhibition of RIP kinase activity with an IC$_{50}$ between about 5 μM and 10 μM and an inhibition of HCMV with an IC$_{50}$ between about 12 μM and 15 μM, respectively. The IC$_{50}$ values of HCMV inhibition were obtained by the use of at least one assay protocol selected from a) virus replication assay, b) plaque assay, c) GFP infection assay, and d) indirect immunofluorescence analysis as disclosed in example 12.

Thus, the three compounds F to H mentioned below and/or pharmaceutically acceptable salts thereof can be used as inhibitors of the cellular protein kinase RIP and as pharmaceutically active compounds for the treatment and/or prophylaxis of HCMV infection. Furthermore, these compounds are suitable for the manufacture of a pharmaceutical composition for prophylaxis and/or treatment of Cytomegalovirus infection and/or diseases associated therewith.

TABLE 2

Inhibitors of RIP and HCMV

| compound | structure | IC$_{50}$ RIP | IC$_{50}$ HCMV |
|---|---|---|---|
| F<br>AX 3646<br>ID 14 | (structure) | 5 μM | 15 μM |
| G<br>AX 3597<br>ID60 | (structure) | 10 μM | 15 μM |
| H<br>AX 6333<br>ID71 | (structure) | 5 μM | 12 μM |

The compounds F to H have the following names:
Compound F: 2-(3,4-Dihydroxyphenyl)-3,5,7-trihydroxychromen-4-one;
Compound G: 5-Cloro-3-(1H-pyrrol-2-ylmethylene)-1,3-dihydroindol-2-one;
Compound H: 4-Quinolin-4-ylmethylene-4H-isoquinoline-1,3-dione.

From the results observed with the compounds shown in Table 2 it is proved that RIP is an important target for the treatment of HCMV and diseases associated with HCMV infection. Inhibitors of the human cellular protein kinase RIP may serve as new pharmaceutical substances for prophylaxis and/or treatment of Cytomegalovirus infection and/or diseases associated with CMV infection.

In addition to the chemical validation of RIP described above, a genetic validation of RIP in HCMV infection was performed. Wildtype and mutated RIP was expressed in HFF cells with a modified Adenovirus as vehicle (Example 9). The expression of mutated RIP, but not wildtype RIP, caused a dramatic reduction in HCMV replication (cf. FIG. 1). These data also confirm RIP a therapeutic target in HCMV treatment.

As known in the art and as used herein, "NIK" (Nck-Interacting Kinase; also known as "HGK" or "MAP4K4") refers to an NF-kappaB inducing serine/threonine kinase that interacts with the SH3 domains of Nck (an adaptor protein composed of one SH2 and three SH3 domains, known as a common target for a variety of cell surface receptors). NIK is most homologous to the Sterile 20 (Ste20) family of protein kinases, particularly GCK and MSST1 in that they bind neither Cdc42 nor Rac and contain an N-terminal kinase domain with a putative C-terminal regulatory domain. NIK is reported to promote neurite process formation and mediated anti-apoptotic signaling. NIK expression leads to IKK activation and induced nuclear translocation of NF-kappaB. NIK activates MEK1 phosphorylation and induces the Erk1/Erk2 MAPK pathway. NIK has been shown to be a MEK1-dependent activator of the MAPK pathway (Foehr et al., 2000. *J. Biol. Chem.* 275, 34021–34024). Overexpression of NIK has been reported to specifically activate the stress-activated protein kinase (SAPK) pathway; possibly upstream of MEKK1, a dominant-negative MEK kinase 1 capable of blocking NIK activation of SAPK (Su et al., 1997. *EMBO* 16(6):1279–90).

As known in the art and as used herein, "MKK3"(MAP kinase kinase 3; also known as "MEK3") refers to a protein kinase known to function in TNF-induced cytokine expression, and specifically phosphorylate and activate p38 MAP kinase (Blank et al., 1996. *J. Biol. Chem.* 271:5361–5368; Raingeaud et al., 1996. *Mol. Cell. Biol.* 16(3):1247–55). MKK3 gene disruption has been shown to cause a selective defect in the response of fibroblasts to the proinflammatory cytokine tumor necrosis factor, including reduced p38 MAP kinase activation and cytokine expression; suggesting that the MKK3 protein kinase is a critical component of a tumor necrosis factor-stimulated signaling pathway that causes increased expression of inflammatory cytokines (Wysk et al., 1999. *PNAS USA* 96(7):3763–8).

As known in the art and as used herein, "SRPK-2"(SR-protein-specific kinase 2) refers to a kinase known to phosphorylate SF2/ASF and believed to regulate the disassembly of the SR family of splicing factors in a tissue-specific manner (e.g., in testis, lung, and brain; Kuroyanagi et al., 1998. *Biochem. Biophys. Res. Commun.* 242(2):357–64). SRPK-2 is believed to function in spliceosome assembly and in mediating the trafficking of splicing factors (Wang et al., 1998. *J. Cell. Biol.* 140(4):737–50; Wang et al., 1999. *Genomics* 57(2):310–5).

In one embodiment, the present invention is directed to a method for treating CMV infection by administering a pharmaceutically effective amount of an inhibitor of one or more of the cellular kinases; RICK, RIP, NIK, MKK3, and/or SRPK-2.

As used herein, a cellular kinase "inhibitor" refers to any compound capable of downregulating, decreasing, suppressing or otherwise regulating the amount and/or activity of a cellular kinase. Inhibition of these cellular kinases can be achieved by any of a variety of mechanisms known in the art, including, but not limited to binding directly to the cellular kinase polypeptide (e.g., a RICK-inhibitor compound binding complex, or substrate mimetic), denaturing or otherwise inactivating the cellular kinase, or inhibiting the expression of the gene (e.g., transcription to mRNA, translation to a nascent polypeptide, and/or final polypeptide modifications to a mature protein), which encodes the cellular kinase. Generally, cellular kinase inhibitors may be proteins, polypeptides, nucleic acids, small molecules, or other chemical moieties.

Yet another aspect of the present invention is directed to pharmaceutical compositions useful for the prophylaxis and/or treatment of an individual afflicted with Cytomegalovirus infection and/or associated diseases. Said pharmaceutical composition comprises at least one pharmaceutically active compound capable of regulating at least partially the activity or the expression of one human cellular protein kinase selected from the group comprising RICK, RIP, NIK, MKK3, and SRPK-2 and/or capable of regulating the replication of CMV.

As used herein the term "regulating" refers either to the ability of an inhibitor to downregulate, decrease, reduce, suppress, inactivate, or inhibit at least partially the activity of an enzyme, or the expression of an enzyme and the virus replication or to the ability of an activator to upregulate, increase, stimulate, or activate at least partially the activity of an enzyme or the expression of an enzyme.

Suitable examples for inhibitors which are the pharmaceutically active components within the therapeutic compositions are the compounds A to H mentioned in Table 1 and 2. The compounds 6-(2,6-Dichlorophenyl)-8-methyl-2-(3-morpholin-4-yl-propylamino)-8H-pyrido[2,3-d]pyrimidin-7-one; 8-methyl-6-phenyl-2-(pyridin-4-yl-amino)-8H-pyrido[2,3-d]pyrimidin-7-one; 6-(2,6-Dichlorophenyl)-8-methyl-2-[3-(4-methylpiperazin-1-yl)-propylamino]-8H-pyrido[2,3-d]pyrimidin-7-one; 4-[5-(3-lodophenyl)-2-(4-methanesulfinylphenyl)-3H-imidazol-4-yl]-pyridine; (3-Bromophenyl)-(6,7-dimethoxyquinazolin-4-yl)-amine; (3-Bromophenyl)-(6,7-diethoxyquinazolin-4-yl)-amine; 2-(3,4-Dihydroxyphenyl)-3,5,7-trihydroxychromen-4-one; 5-Cloro-3-(1H-pyrrol-2-ylmethylene)-1,3-dihydroindol-2-one; 4-Quinolin-4-ylmethylene-4H-isoquinoline-1,3-dione; 2,3,7,8-Tetrahydroxychromeno[5,4,3-cde]chromene-5,10-dione; 3-(1H-Pyrrolo[2,3-b]pyridin-3-ylmethylene)-1,3-dihydropyrrolo[2,3-b]pyridin-2-one and/or pharmaceutically acceptable salts of these compounds are useful for prophylaxis and/or treatment of Cytomegalovirus infection and/or diseases associated with Cytomegalovirus infection.

CMV therapeutics may be administered to cells from an individual in vitro, or may involve in vivo administration to the individual. Routes of administration of pharmaceutical preparations to an individual may include inhalation, oral and parenteral, including dermal, intradermal, intragastral, intracutan, intravasal, intravenous, intramuscular, intraperitoneal, intranasal, intravaginal, intrabuccal, percutan, rectal, subcutaneous, sublingual, topical or transdermal application, but are not limited the these ways of administration. For instance, the preferred preparations are in administratable form which is suitable for oral application. These administratable forms, for example, include pills, tablets, film tablets, coated tablets, capsules, powders and deposits. Administration to an individual may be in a single dose or in repeated administrations, and may be in any of a variety of physiologically acceptable salt forms, and/or with an acceptable pharmaceutical carrier, binder, lubricant, excipient, diluents and/or adjuvant. Pharmaceutically acceptable salt forms and standard pharmaceutical formulation techniques are well known to persons skilled in the art (see, for example, Remington's Pharmaceutical Sciences, Mack Publishing Co.).

As used herein, a "pharmaceutically effective amount" of a cellular kinase inhibitor is an amount effective to achieve the desired physiological result, either in cells treated in vitro or in a subject treated in vivo. Specifically, a pharmaceutically effective amount is an amount sufficient to inhibit, for some period of time, one or more of the clinically defined pathological processes associated with the viral infection. The effective amount may vary depending on the specific kinase inhibitor selected, and is also dependent on a variety of factors and conditions related to the subject to be treated and the severity of the infection. For example, if the inhibitor is to be administered in vivo, factors such as the age, weight and health of the patient as well as dose response curves and toxicity data obtained in preclinical animal work would be among those considered. If the inhibitor is to be contacted with the cells in vitro, one would also design a variety of pre-clinical in vitro studies to assess such parameters as uptake, half-life, dose, toxicity, etc. The determination of a pharmaceutically effective amount for a given agent is well within the ability of those skilled in the art.

As a result of the discovery of the upregulation of certain cellular kinases as part of the infection process of CMV, a novel diagnostic assay useful for the detecting CMV infection of an individual (or cell) is identified. The diagnostic assay of the present invention involves providing a sample from an individual or providing cells and/or cell lysates, and detecting activity in the sample of one or more cellular kinases selected from the group consisting of RICK, RIP, NIK, MKK3, and SRPK-2. In one embodiment, deviations in the expression levels of one or more of the identified cellular kinases in a test sample compared to a known normal expression levels (e.g., determined from a sample from a healthy individual) will be diagnostic of CMV.

It is apparent to a practitioner in the art that a sample useful for detecting CMV infection, whether of a subject individual or an isolated cell, refers to any cellular extract (including whole cells) from a tissue or body fluid (in the case of an individual) or cellular lysate (in the case of an isolated cell), which contains cellular components representative of cellular activity of one or more of the above-mentioned cellular kinases.

It is also apparent to a person of ordinary skill in the art that detection includes any method known in the art useful to indicate the presence, absence, or amount of a detection target. Such methods may include, but are not limited to, any molecular or cellular techniques, used singularly or in combination, including, but not limited to: hybridization and/or binding techniques, including blotting techniques and immunoassays; labeling techniques (chemiluminescent, colorimetric, fluorescent, radioisotopic); spectroscopic techniques; separations technology, including precipitations, electrophoresis, chromatography, centrifugation, ultrafiltration, cell sorting; and enzymatic manipulations (e.g., digestion).

Because the present disclosure teaches for the first time the upregulation of a group of cellular kinases specifically involved in the viral infection of CMV, the present invention is also directed to an assay useful for detecting novel compounds useful for treating CMV infection.

Assays of the present invention identify compounds useful for treating CMV operate by screening a test compound, or library of test compounds, for its ability to inhibit any one or more of the group of cellular kinases identified herein as characteristically upregulated during CMV growth and replication inside a cell. A variety of assay protocols and detection techniques are well known in the art and easily adapted for this purpose by a skilled practitioner. Such assays include, but are not limited to, high throughput assays (e.g., microarray technology, phage display technology), and in vitro and in vivo cellular and tissue assays.

In a related aspect, it is also an object of the present invention, in view of the discovery of cellular kinases specifically involved in CMV growth in a cell, to provide an assay component specially useful for detecting CMV in an individual (or a cell). Preferably the assay component comprises oligonucleotides capable of detecting activity of one or more of the cellular kinases RICK, RIP, NIK, MKK3, and SRPK-2 in a sample (e.g., by hybridization to mRNA from the sample), immobilized on a solid support. Most preferably the solid support would contain oligonucleotides of sufficient quality and quantity to detect all of the above-mentioned cellular kinases (e.g., a nucleic acid microarray).

Similarly, it is part of the object of the invention to provide an assay component specially useful for screening compounds useful for treating CMV. One preferred assay component comprises oligonucleotides that encode one or more of the cellular kinases RICK, RIP, NIK, MKK3, and SRPK-2, immobilized on a solid support. In another embodiment, the assay component comprises peptide fragments of one or more of the above-identified cellular kinases immobilized on a solid support. Once again the most preferred solid support embodiment would contain polymers of sufficient quality and quantity to detect all of the above-mentioned cellular kinases (e.g., a nucleic acid or a peptide microarray). A variety of assay supports and construction of the same are well known in the art and easily adapted for this purpose by a skilled practitioner (see, for example: Marshall, 1999. "Do-it-yourself gene watching" *Science* 286:444–447 (including insets); and Service, 2000. "Protein arrays step out of DNA's shadow" *Science* 289:1673).

It is preferred that mRNA is assayed as an indication of expression. Methods for assaying for mRNA include, but are not limited to, Northern blots, slot blots, dot blots, and hybridization to an ordered array of oligonucleotides. Nucleic acid probes useful for assay of a sample are preferably of sufficient length to specifically hybridize only to appropriate, complementary transcripts. Typically the oligonucleotide probes will be at least 10, 12, 14, 16, 18, 20 or 25 nucleotides in length. In some cases longer probes of at least 30, 40, or 50 nucleotides will be desirable.

The cDNA oligonucleotides immobilized on said membrane filter which are used for detecting the up- or down-regulation of the above-mentioned human cellular protein kinases by hybridization to the radioactively labeled cDNA probes have the nucleotide sequences listed in table 3.

TABLE 3

Nucleotide sequences of cDNA-arrays

| Human cellular kinase | Sequence of immobilized DNA on arrays (in relation to the respective Acc No) |
| --- | --- |
| RICK | 914 bp–2501 bp (AF027706) |
| RIP | 1421 bp–2617 bp (U50062) |
| NIK | 231 bp–3077 bp (Y10256) |
| MKK3 | 341 bp–2030 bp (NM_002756) |
| SRPK-2 | 1238 bp–2790 bp (U88666) |

The nucleoside sequences of the genes coding for the human cellular protein kinases RICK, RIP, NIK, MKK3, and SRPK-2 listed in Table 3 together with the amino acid sequences of said enzymes can be obtained from NCBI (National Library of Medicine: PubMed; Web address: www.ncbi.nlm.nih.gov/entrez). Sequence protocols of the five cellular protein kinases are attached to this application as a part of the description.

The polypeptide product of gene expression may be assayed to determine the amount of expression as well. Methods for assaying for a protein include, but are not limited to, Western blot, immunprecipitation, radioimmunoassay and peptide immobilization in an ordered array. It is understood, however, that any method for specifically and quantitatively measuring a specific protein or mRNA product can be used.

A variety of supports upon which nucleic acids or peptides can be immobilized are known in the art, for example filters, or polyvinyl chloride dishes. Any solid surface to which oligonucleotides or peptides can be bound, either directly or indirectly, either covalently or non-covalently, can be used. A preferred solid support is a microarray membrane filter or a "biochip". These contain particular polymer probes in predetermined locations on the array. Each predetermined location may contain more than one molecule of the probe, but each molecule within the predetermined location has an identical sequence.

The present invention incorporates by reference in their entirety techniques well known in the field of molecular biology. These techniques include, but are not limited to, techniques described in the following publications:

Ausubel, F. M. et al. eds., *Short Protocols In Molecular Biology* (4th Ed. 1999) John Wiley & Sons, NY. (ISBN 0-471-32938-X).

Old, R. W. & S. B. Primrose, *Principles of Gene Manipulation: An Introduction To Genetic Engineering* (3d Ed. 1985) Blackwell Scientific Publications, Boston. Studies in Microbiology; V. 2:409 pp. (ISBN 0-632-01318-4).

Miller, J. H. & M. P. Calos eds., *Gene Transfer Vectors For Mammalian Cells* (1987) Cold Spring Harbor Laboratory Press, NY. 169 pp. (ISBN 0-87969-198-0).

Mayer, R. J. & J. H. Walker eds., *Immunochemical Methods In Cell and Molecular Biology* (1987) Academic Press, London. 325 pp. (ISBN 0-12480-855-7).

Sambrook, J. et al. eds., *Molecular Cloning: A Laboratory Manual* (2d Ed. 1989) Cold Spring Harbor Laboratory Press, NY. Vols. 1–3. (ISBN 0-87969-309-6).

Winnacker, E. L. *From Genes To Clones: Introduction To Gene Technology* (1987) VCH Publishers, NY (translated by Horst Ibelgaufts). 634 pp. (ISBN 0-89573-614-4).

The present invention further incorporates by reference in their entirety techniques well known in the field of microarray construction and analysis. These techniques include, but are not limited to, techniques described in the following patents and patent applications describing arrays of biopolymeric compounds and methods for their fabrication: U.S. Pat. Nos. 5,242,974; 5,384,261; 5,405,783; 5,412,087;

5,424,186; 5,429,807; 5,436,327; 5,445,934; 5,472,672; 5,527,681; 5,529,756; 5,545,531; 5,554,501; 5,556,752; 5,561,071; 5,599,895; 5,624,711; 5,639,603; 5,658,734; 5,807,522; 6,087,102; WO 93/17126; WO 95/11995; WO 95/35505; EP 742 287; and EP 799 897. Techniques also include, but are not limited to, techniques described in the following patents and patent application describing methods of using arrays in various applications: U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,994,076; 6,033,860; 6,040,138; 6,040,140; WO 95/21265; WO 96/31622; WO 97/10365; WO 97/27317; EP 373 203; and EP 785 280.

It is readily apparent to those skilled in the art that other suitable modifications and adaptations of the compositions and methods of the invention described herein are obvious and may be made without departing from the scope of the invention or the embodiments disclosed herein. Having now described the present invention in detail, the same will be more clearly understood by reference to the following examples, which are included for purposes of illustration only and are not intended to be limiting of the invention.

EXAMPLES

Materials and Methods

Example 1
Signal Transduction cDNA Microarray Construction

To study the cellular pathology associated HCMV, a unique microarray of more than 1100 signal transduction cDNAs was created.

In order to manufacture cDNA-arrays on membranes, the following strategy was employed: cDNAs encoding parts of or full length proteins of interest (referred to as "target cDNAs") were cloned into the plasmid BLUESCRIPT II KS+ (Stratagene, USA). Large scale purifications of these plasmids were performed according to standard techniques, and 200 µl aliquots (1 µg/µl plasmid concentration) were transferred into appropriate 96 well plates. The plates were then sealed with sealing tape, incubated for 10 minutes at 95° C., and chilled on ice for 5 minutes. 10 µl of 0.6N NaOH were added, and the mix was then stored for 20 minutes at room temperature. Following the incubation at room temperature, 10 µl 2.5M Tris-HCl (Tris-(hydroxymethyl)-aminomethane-hydrochloride) pH 7.1 and 20 µl 40 x SSC (6M Sodium chloride—0.6M tri-Sodium citrate buffer) was added.

Target cDNAs were spotted onto Nylon or Nitrocellulose membranes using a BIOGRID (BioRobotics, UK) equipped with a 0.7 mm pintool. 200–350 ng of plasmid-encoding target cDNAs were transferred onto the membranes and crosslinked to the membranes using ultraviolet light ($1.2 \times 10^5$ µJ/cm$^2$) treatment. The arrays were stored for use in subsequent experiments (described below) at room temperature.

Example 2
HCMV Infection

To examine the effects of HCMV infection on cellular signal transduction activity, HCMV-infected cells were generated for comparison to control (i.e., uninfected) cells.

Primary human foreskin fibroblasts (HFF) were grown close to confluency in MEM medium (Minimum Essential Medium, Life Technologies) supplemented with 20% fetal calf serum at 37° C. and 5% $CO_2$ to obtain ~$6\times10^6$ cells per tissue culture flask. Virus adsorption to the cells was performed with the HCMV strain AD169 at different (0.2, 1, and 3) multiplicities of infection (MOI) for 90 minutes in a volume of 5 ml at 37° C. The viral inoculum was removed, and cells were cultured in 50 ml of MEM medium supplemented with 20% fetal calf serum and 150 µg/ml cyclohex-imid at 37° C. and 5% $CO_2$ for 7, 24, 48, or 72 hours, respectively.

Example 3
Isolation and Purification of Poly A+ RNA

In order to perform differential expression analysis using the cDNA microarray described in Example 1, RNA extraction and purification on the HCMV-infected and uninfected cells was performed using techniques known in the art.

Briefly, after incubation (for the respective time-intervals) of infected and control cells, cells were washed twice with phosphate buffered saline (PBS) and then trypsinized. Cells were removed from the culture dish by resuspension with PBS. Cells were then sedimented, and directly lysed by repetitive pipetting in 1 ml of Tri reagent (Molecular Research Centre, Inc., USA) per $1\times10^6$ cells.

Cell lysates were stored at room temperature for 5 minutes, and then centrifuged (12,000×g) for 15 minutes at 4° C. The supernatant was mixed with 0.1 ml of 1-bromo-3-chloropropane per 1 ml of Tri reagent and shaken vigorously. The resultant suspension was stored for 5 minutes at room temperature, and then centrifuged (12,000×g) for 15 minutes at 4° C.

Following centrifugation, the colorless upper phase was transferred into new tubes, mixed with 5 µl of poly-acryl-carrier (Molecular Research Centre, Inc., USA), and vigorously shaken with 0.5 ml of isopropanol per 1 ml of Tri reagent. The samples were stored at room temperature for 5 minutes and then centrifuged (12,000×g) for 8 minutes at 4° C. The supernatant was removed and the RNA pellet washed twice with 1 ml of 75% ethanol. The pellet was dried and resuspended in RNase-free buffer at a concentration of 1 µg RNA per 1 µl buffer.

Purification of poly A+ RNA from total RNA was performed using the OLIGOTEX system (Qiagen, Germany) following manufacturer's instructions. In brief, 100–200 µg of total RNA was brought up to 250 µl with RNase-free water, and 250 µl of buffer OBB (20 mM Tris/HCl pH7.5, 1M NaCl, 2 mM EDTA, 0.2% SDS) and 15 µl of OLIGOTEX suspension was added. The samples were incubated for 3 minutes at 70° C., and placed at room temperature for 10 minutes. The samples were centrifuged for 2 minutes (12,000×g), and the supernatant removed. The remaining pellet was resuspended in 400 µl buffer OW2 (10 mM Tris/HCl pH 7.5, 150 mM NaCl, 1 mM EDTA). The suspension was transferred to a spin column (supplied with the system) and centrifuged at 12000×g for 1 minute at room temperature. The spin column was transferred to a new tube and 400 µl of buffer OW2 was applied on the column. The spin column was centrifuged (12,000×g) for 1 minute at room temperature. The spin column was transferred to a new tube and the RNA eluted from the column by the addition of 50 µl buffer OEB (5 mM Tris/HCl pH7.5) (at 70° C.) to the column, resuspension of the Oligotex-resin, and centrifugation (12,000×g) for 1 minute at room temperature.

Any genomic DNA contamination of the RNA preparations was eliminated by enzymatic digestion using DNase I. 6 µl of 10×DNase buffer (Promega, USA) and 4 µl of RQ-DNase (Promega, USA) were added to 50 µl of the RNA-buffer solution, and the reaction mixture was incubated for 15 minutes at 37° C. Stop-buffer (6 µl Promega, USA) was then added, the mixture brought to 200 µl final volume with TE buffer (10 mM Tris/HCl, 1 mM EDTA), and Phenol/Chloroform extractions were performed twice. The RNA-containing phase was transferred to new reaction tubes and RNA was precipitated using 5M NaCl (final concentration of 0.2M), 1 μl poly-acryl-carrier (Molecular Research Centre, Inc., USA) and 500 μl of 100% ethanol. The solution was centrifuged for 10 minutes at 4° C., the RNA pellet washed with 1 ml of 80% ethanol, dried, and resuspended in 30 μl TE buffer. Poly A$^+$ RNA suspension samples were stored at −70° C. for use in subsequent experiments.

Example 4

Preparation of Radioactively Labeled cDNA Probes from RNA

To prepare test and control samples for microarray analysis, RNA samples isolated and purified from HCMV-infected and control cells (prepared as described in Example 3) were used to generate radioactively labeled cDNA probe. Many techniques to generate labeled cDNA constructs from cellular RNA extracts are known in the art and applicable to the present invention. Two of those protocols were used in this example to generate radiolabeled cDNA from RNA samples: the first technique involved reverse transcribing cDNA from the RNA sample in the presence of radioactively labelled dATP; the second technique involved first strand cDNA synthesis from the RNA sample, followed by random priming with radioactively labelled dATP.

For reverse transcription of cDNA from the RNA sample in the presence of radioactively labelled dATP, 1 μg of primer TXN (5'-TTT TTT TTT TTT TTT TXN-3'; SEQ ID NO:1; with T=dTTP; N=dATP, dCTP, dGTP or dTTP; X=dATP, dCTP or dGTP) and total RNA (1 to 15 μg) or poly A$^+$ RNA (20 to 500 ng) were combined in 12 μl bidistilled DEPC-treated H$_2$O (DEPC: diethylpyrocarbonate) and shaken for 5–15 minutes at 60° C. The mixture was then incubated at 4° C. for 2–10 minutes, and centrifuged (10,000×g) for 30 seconds.

After centrifugation, 7 μl of a labelling mix (100 μCi γ[$^{33}$P]-ATP (Amersham, UK); vacuum dried and resuspended in 4 μl first strand buffer (Life Technologies, USA); 2 μl 0.1M DTT (dithiothreitol); and 1 μl labelling solution—4 mM dCTP, dGTP, dTTP each and 80 μM dATP final concentration) was added to the RNA solution. 1 μl SUPERSCRIPT II reverse transcriptase (Life Technologies, USA) was added and the reaction incubated for 10 minutes at room temperature and then for 60 minutes at 38° C. Following the reaction incubation, 5 μl 0.5M EDTA (ethylene diamine tetraacetate) and 25 μl 0.6M NaOH was added to the reaction mixture and shaken vigorously for 30 minutes at 68° C.

Unincorporated nucleotides were removed from the labelling reaction using PROBEQUANT G-50 columns (Amersham, UK). The column (with bottom closure and lid removed) was shaken vigorously and centrifuged (735×g) for 1 minute in an appropriate reaction tube. The column was placed into a new reaction tube, the probe was applied onto the center of the column material and the column was centrifuged (735×g) for 2 minutes. The flow-through was transferred into new reaction tubes and bidistilled H$_2$O added to 100 μl final volume. 5M NaCl, 1 μl poly-acryl-carrier (Molecular Research Centre, Inc., USA) and 250 μl ethanol was added, and the probe precipitated by centrifugation (12,000×g) for 15 minutes. The supernatant was discarded and the pellet dried for subsequent use.

For the alternate labelling technique (random priming with radioactively labelled dATP after first strand cDNA synthesis), the following procedure was followed: 1 μg primer TXN (see above) was added to 20–500 ng of poly A$^+$ RNA in 12 μl final volume, incubated for 5 minutes at 60° C., followed by an addition incubation for 2–10 minutes on ice. The mix was centrifuged (12,000×g) for 30 seconds, and 4 μl of first strand buffer (Life Technologies, USA), 2 μl 0.1M DTT, 1 μl 10 mM dNTP and 1 μl SUPERSCRIPT II reverse transcriptase (Life Technologies, USA) was added. The reaction was incubated for 10 minutes at room temperature, followed by an additional incubation for 60 minutes at 38° C. Following the reaction incubation, 5 μl 0.5M EDTA and 25 μl 0.6M NaOH was added to the reaction mixture and shaken vigorously for 30 minutes at 68° C.

Unincorporated nucleotides were removed as described above; however, the final pellet was resuspended in 30 μl bidistilled H$_2$O.

15 μl of the resuspended cDNA solution was transferred to new reaction tubes, incubated for 5 minutes at 95° C., chilled on ice for 5 minutes, and centrifuged for 30 seconds. Following manufacturer's instructions accompanying the Random Primers DNA Labelling system (Life technologies, USA), 15 μl buffers mixture, 2 μl of each dCTP, dGTP and dTTP (provided with the system) were added to the cDNA. 5 μl γ[$^{33}$P]-ATP (Amersham, UK) was added and the mixture adjusted to 49 μl final volume with bidistilled H$_2$O. The reaction was started by addition of 1 μl Klenow enzyme (supplied with the system), and incubated for 60 minutes at 25° C. 5 μl. Stop solution (provided with the system) was added and unincorporated nucleotides were removed by column purification as described above.

Example 5

Hybridization of Labeled cDNA Probe to cDNA Array

To screen HCMV-infected cells compared to uninfected cells for differential activation of cellular signal transduction, labeled cDNA probes (generated according to Example 4) were exposed to a signal transduction cDNA microarray (generated as described in Example 1) following hybridization techniques known in the art.

Sample pellets from Example 4 were resuspended in 10 μl C$_0$T DNA (1 μg/μl, Roche Diagnostics, Germany), 10 μl yeast tRNA (1 μg/μl Sigma, USA) and 10 μl poly A (1 μg/μl, Roche Diagnostics, Germany). Herring sperm DNA (to a final concentration of 100 μg/ml), 5 μl 10% SDS (Sodiumdodecylsulfate), and 25 μl 20×SSPE was added, and adjusted 100 μl final volume with bidistilled H$_2$O. The mix was incubated for 5 minutes at 95° C., centrifuged (10,000× g) for 30 seconds, and vigorously shaken for 60 minutes at 68° C. A 1 μl aliquot of the probe was used to measure the incorporation of radioactive dATP with a scintillation counter. Probes with at least a total of 20×10$^6$ cpm were used for the screen assay.

Arrays were prehybridized in hybridization solution for at least 30 minutes in a roller bottle oven at 42° C. Following prehybridization, radiolabelled probe was added to the hybridization solution and hybridization was continued for 20–40 hours.

Following hybridization, the probe was discarded and the array subjected to a series of washes. Initially the arrays were washed twice in wash solution A (2×SSC) in the roller oven at room temperature. Wash solution A was then replaced with wash solution B (2×SSC, 0.5% SDS), preheated to 60° C., and arrays were washed twice for 30 minutes at 60° C. Wash solution B was then replaced with wash solution C (0.5×SSC, 0.5% SDS), preheated to 60° C., and arrays were washed twice for 30 minutes at 60° C.

The moist arrays were wrapped in airtight bags and exposed for 8–72 hours on erased phosphoimager screens (Fujifilm, Japan).

Example 6
Signal Transduction cDNA Array Analysis

To demonstrate differential activation of cellular signal transduction in HCMV-infected cells compared to uninfected cells, hybridized cDNA arrays from infected and uninfected samples were analyzed.

Exposed phosphoimager screens (from Example 5) were scanned with a resolution of 100µ and 16 bits per pixel using a BAS-1800 (Fujifilm, Japan). The data were imported into the computer program, ARRAYVISION (Imaging Research, Canada), and analyzed according the computer program's specification. Hybridization signal strength is indicative of the quantity of RNA molecules present in the probe. Differentially expressed genes were identified according to the ratio of signal strength after normalization to the overall intensity of the arrays.

Signal transduction cDNA microarray analysis of radiolabelled cDNA-probes from HCMV-infected (strain AD169) versus non-infected primary human foreskin fibroblasts to cDNA-arrays revealed significant upregulation of the cellular kinase cDNAs:

RICK (2-fold at 3 hours post infection; 3.6-fold at 7 hours post infection);

RIP (2.6-fold at 3 hour post infection; 2.2-fold at 24 hour post infection);

NIK (4-fold at 7 hour post infection);

MKK3 (2-fold at 3 hour post infection; 2.5-fold at 7 hour post infection); and

SRPK-2 (2.2-fold at 7 hour post infection)

compared to uninfected human foreskin fibroblasts cells.

Example 7
Northern Blot Analysis

To confirm the results of the microarray analysis of Example 6, northern blot analysis was performed according to techniques well known in the art.

HCMV-infected and uninfected cells (from Example 2) cells were pelleted and the total RNA was prepared as follows: Following centrifugation and removal of the supernatant, cells were lysed in 1 ml of Trizol reagent (ready-to-use-reagent from Gibco-BRL) per 1.5 $10^6$ cells. The Tri reagent/cell lysate was transferred to an eppendorff tube and centrifuged (13,000 rpm) for 15 minutes at 4° C. The supernatant was transferred to a new eppendorff tube and 0.1 ml of BCP (1-bromo-3-chlorpropane) for each ml of Tri reagent was added. Samples were vortexed for 15 seconds, incubated for 5 min at room temperature, and then centrifuged (13,000 rpm) for 15 minutes at 4° C. The upper aqueous phase was transferred to a new eppendorff tube, 0.5 ml isopropanol was added for each ml of Tri reagent (Molecular Research Center, Inc., USA), vortexed, and incubated for additional 8 min at room temperature, and centrifuged (13,000 rpm) for 10 min at 4° C. The supernatant was aspirated, and the precipitated RNA was washed twice with ice-cold 75% ethanol and air-dried. The RNA pellet was resuspended in 50 µl Tris-HCl pH 7.5.

The quantity of the RNA for each sample was determined by UV-spectroscopy, and the quality was determined via gel electrophoresis on a formaldehyde-containing 1.2% agarose gel.

RNA samples of 10 µg each were size-fractionated by 1.2% formaldehyde agarose gel electrophoresis and transferred to synthetic membrane filters (Hybond N, Amersham) with 20×SSC (1×SSC is 150 mM NaCl, 15 mM $C_6H_5Na_3O_7 \times 2H_2O$, pH 7.0) overnight. RNA was immobilized to the filter using UV-light for crosslinking (120 mJ/cm$^2$ for 25 seconds).

Membrane filters were firstly prehybridized for 4 hours at 65° C. in a prehybridization solution containing 5×SSC, 10×Denhardt's solution (1×Denhardt's solution is 0.02% bovine serum albumine, 0.02% polyvinyl pyrrolidone, 0.02% ficoll), 20 mM sodium phosphate, pH 7.0, 7% SDS, 100 µg/ml sonicated salmon sperm DNA, and 100 µg/ml. Hybridization was performed at 65° C. in the prehybridization buffer containing 10% dextran sulphate, plus added radiolabelled probe for 16 hours.

Membrane filters were hybridized to oligonucleotide probes specific for a particular cellular kinase identified in Example 6. Probes sequences included the following:

TABLE 4

| Cellular Kinase | cDNA Probe Sequence | SEQ ID NO: |
|---|---|---|
| NIK | 5'-GTC CTG GAG GGC TCT TTT TGA TGA AAC C-3' | 2 |
| RIP | 5'-GTG CTC AAT GCA GTT GGG CCC CTT GTA CAC-3' | 3 |
| RICK | 5'-GTC GAG CAG CGG AGT GTG GAT GTG CAG-3' | 4 |

The oligonucleotides were radiolabelled at their 3' ends with (alpha-32P) deoxyadenosine 5'-triphosphate ($^{32}$P-α-dATP) (Amersham) employing the Terminal Transferase kit (Roche) following manufacturer's instructions.

Unincorporated $^{32}$P-α-dATP nucleotides were removed similar to the protocol described in Example 4: After vortexing the PROBEQUANT Sephadex G-50 (Amersham, UK) column (with bottom closure and lid removed), the column was placed in a 2 ml tube and centrifuged for 1 minute at 735×g. The column was placed in a new 1.5 ml eppendorff tube (without a cap), and the radioactive probe was pipetted carefully on the center of the preformed resin. Centrifugation (735×g) for 2 minutes effectively removed the unincorporated $^{32}$P-α-dATP nucleotides.

Hybridized filters were washed once in 5% SDS, 3×SSC, 10×Denhardt's solution, 20 mM sodium phosphate, pH 7.0 for 30 min at 65° C. A second wash step followed in 1×SSC, 1% SDS at 65° C. for 30 min.

Filters were exposed at −80° C. to Kodak XAR-5 films using intensifying screens.

Northern blot analysis confirmed upregulation of cellular kinase mRNA: RICK, RIP, and NIK in HCMV-infected cells compared to uninfected cells, consistent with results obtained from microarray analysis.

Example 8
Western Blot Analysis

To further confirm the results of the microarray analysis of Example 6 and northern blot analysis of Example 7, western blot analysis was performed according to techniques well known in the art.

HCMV-infected and uninfected cells (from Example 2) were pelleted and polypeptide extracts prepared as follows: Infected and uninfected cell samples (from various time intervals) were lysed with 420 µl of lysis buffer (20 mM Hepes (N-[2-hydroxyethyl]piperazine-N'-[2-ethansulfonic acid]) pH7.5, 150 mM NaCl, 1% TRITON X-100 (t-octylphenoxypolyethoxyethanol), 10% glycerol, 1 mM PMSF (phenylmethylsulfonyl fluoride), 10 µg/ml Aprotinin, 1 mM ortho-vanadat) on ice. Lysed cells were cleared from debris by centrifugation (15 minutes, 13000 rpm, 4° C.), dissolved in 1×Laemmli buffer, denatured for 5 minutes at 100° C. and submitted to SDS-PAGE (gradient gel 7%–12%).

Gels were blotted onto nitrocellulose filters (Amersham, UK) for 3 hours (0.8 mA/cm$^2$). Detection of expression of the identified host cell kinases was performed using the following target specific antibodies: OPA1-01023 polyclonal rabbit anti-RICK antibody (Dianova); H-207 polyclonal rabbit anti-RIP antibody (Santa Cruz Biotechnology); I-20 polyclonal rabbit anti-MKK3 antibody (Santa Cruz Biotechnology); S80620 murine anti-SRPK2 antibody (Transduction Laboratories); anti-NIK rabbit serum (generated by SIGMA Genosys Biotechnologies using the NIK-peptide 5'-CNPTNTRPQSDTPEIRKYKKRFN-3', SEQ ID NO:5, for immunization). All antibodies were used according to the manufacturer's instructions. Detections were performed with the ECL Kit (Amersham, UK).

Western blot analysis confirmed the transcriptional upregulation of infected host cell kinase mRNAs resulted in increased expression of the respective proteins:

A single ~60 kDa band representing RICK was upregulated between 7–24 hours post HCMV infection;

A single ~74 kDa band representing RIP was upregulated between 7–72 hours post HCMV infection;

A single ~135 kDa band representing NIK was upregulated between 24–72 hours post HCMV infection;

A single ~35 kDa band representing MKK3 was upregulated between 7–72 hours post HCMV infection; and A single ~115 kDa band representing SRPK2 was upregulated between 24–72 hours post HCMV infection.

Example 9

Genetic Validation

HFF cells were infected with Adenovirus expressing various kinase constructs at different particles per cell ratios (p/c). The adenovirus used here were all E1, E3 defective derivatives of adenovirus type 5 (reviewed in Russell WC (2000) Update on adenovirus and its vectors. J Gen Virol. 81:2573–604). Briefly, the cDNA of interest was cloned into a transfer plasmid bearing the CMV IE promoter enhancer (IE: immediate early) and the rabbit beta-globin intron/polyadenylation signal. This expression cassette was inserted into a bacterial plasmid borne-adenovirus genome using recombination in bacteria (Chartier C., E. Degryse, M. Gantzer, A. Dieterle, A. Pavirani, and M. Mehtali. 1996. Efficient generation of recombinant adenovirus vectors by homologous recombination in *Escherichia coli*. J. Virol. 70:4805–4810.). Virus was amplified in HEK 293 cells and purified from cell lysates using CsCl density gradient centrifugation as described (Cotten, M., Baker A., Birnstiel M. L., Zatloukal, K., Wagner, E. (1996) Adenovirus polylysine DNA conjugates. in Current Protocols in Human Genetics, Eds. N. C. Dracopoli, J. L. Haines, B. R. Korf, D. T. Moir, C. C. Morton, C. E. Seidman, J. G. Seidman, D. R. Smith; John Wiley and Sons, Inc. New York. pp. 12.3.1–12.3.33.). The control viruses AdJ5 was previously described (Glotzer J. B., Saltik M., Chiocca S., Michou A. I., Moseley P. and Cotten M. (2000) Activation of heat-shock response by an adenovirus is essential for virus replication. Nature 407:207–11).

Two days after plating HFF cells, cultures were infected with CMV strain Ad169-GFP. Replication of CMV was estimated after one week (7 dpi) utilizing the GFP-signal expressed as GFP counts.

FIG. 1 shows the reduction rates in HCMV replication of HHF cells pre-infected with Adeno virus containing the RIP wildtype sequence (AdRIPwt; 1–4) and a RIP inactive mutant (AdRIPkr; 5–8).

No HCMV-infection resulted in hardly any signal (mock, 13), while infection with HCMV yielded in about 13.000 GFP counts (AD169-GFP; 14). Pre-infection with increasing amounts of control Adeno virus (AdliteJ5) caused a slight reduction in HCMV replication (9–12). There was a clear difference, when HFF cells were pre-infected with Adeno virus containing the RIP wildtype sequence (AdRIPwt; 1–4) and a RIP inactive mutant (AdRIPkr; 5–8). The lysine (K) at amino acid position 45 is mutated to an arginine (R), which renders the kinase inactive. This mutation was introduced into the human RIP cDNA utilizing the QuikChange™ Site-directed Mutagenesis Kit (Stratagene, Calif., USA) according to the instructions of the manufacturer. Expression of the mutated RIP kinase efficiently blocked HCMV replication (5–8), while the wildtype sequence was less potent in doing so (1–4).

Figure 2:
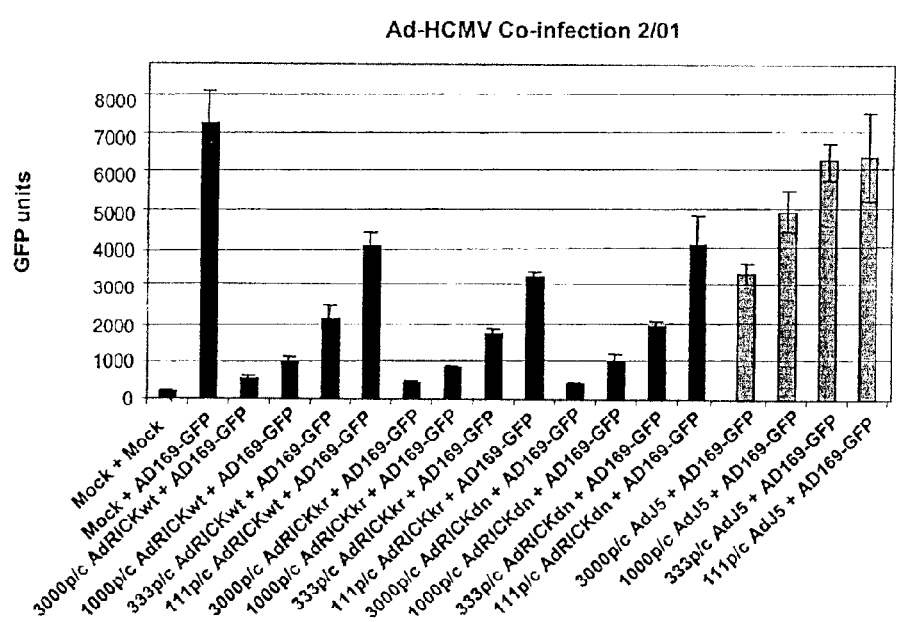
FIG. 2 is a bar graph showing the reduction rates in HCMV replication of HHF cells pre-infected with Adenovirus containing the RICK wildtype sequence (AdRICKwt) and two RICK inactive mutans (AdRICKkr and AdRICKdn).

FIG. 2 shows the reduction rates in HCMV replication of HHF cells pre-infected with Adeno virus containing the RICK wildtype sequence (AdRICKwt) and two RICK inactive mutants (AdRICKkr and AdRICKdn). In one construct (AdRICKkr), the lysine (K) at position 47 is mutated to an arginine (R). In the other construct (AdRICKdn), the aspartate at position 146 is mutated to an asparagine. Both changes in sequence render the kinase inactive. The mutations were introduced into the human RICK cDNA utilizing the QuikChange™ Site-directed Mutagenesis Kit (Stratagene, Calif., USA) according to the instructions of the manufacturer.

Similar experiments as described for RIP (Example 9, FIG. 1) were also performed with RICK. No HCMV-infection resulted in hardly any signal (Mock+Mock), while infection with HCMV yielded in about 7.000 GFP counts (Mock+AD169-GFP). Pre-infection with increasing amounts of control Adeno virus (AdliteJ5, from 111 to 3000 particles per cell) caused a slight reduction in HCMV replication. There was a clear difference, when HFF cells were pre-infected with Adeno virus containing the RICK wildtype sequence (AdRICKwt and two RICK inactive mutants (AdRICKkr and AdRICKdn). All three RICK constructs efficiently reduced HCMV-replication.

Example 10

RICK-Kinase Assay

To obtain active RICK kinase the human RICK-cDNA was fused with a DNA sequence coding for the HA-tag and cloned into the eucaryotic expression vector pcDNA3 (Invitrogene). This construct was transfected into human embryonic kidney cells (HEK 293) via the calcium-phosphate co-precipitation method. One day after transfection medium was replaced by fetal calf serurum-free medium and two days after transfection cells were washed with PBS and harvested and lysed in RIPA-buffer (150 mM NaCl, 1 mM EDTA, 1% Triton X-100, 1% Na-desoxycholate, 0.1% SDS, 10 mM Tris-HCl pH 7.5). The RICK-HA fusion protein was immunoprecipitated from 250 $\mu$l cleared lysate (i.e. lysate of one well of a six-well plate) utilizing an anti-HA antibody from Roche Pharmaceuticals and Protein A sepharose. After addition of 500 $\mu$l of HNTG-buffer (50 mM HEPES pH 7.5, 150 mM NaCl, 1 mM EDTA, 10% glycerine, 0.1% Triton X-100) the sample was rotated for 3 hrs at 4° C. After washing the immunoprecipitate twice with 0.5 ml HNTG-buffer and twice with 0.5 ml assay-buffer (25 mM Tris-HCl pH 7.5, 3 mM MgCl$_2$, 0.5 mM MnCl$_2$, 0.5 mM DTT and 50 mM NaCl), the kinase reaction was performed directly on the beads in 40 $\mu$l assay buffer containing 2.5 $\mu$Ci $\gamma$[$^{33}$P]-ATP and various concentrations (between 100 nM and 50 $\mu$M) of compounds of Table 1. After 30 min at 30° C., the reaction was stopped by addition of 40 $\mu$l 3×Laemmli-buffer (16% glycerol, 1.01M $\beta$-mercaptoethanol, 5% SDS, 200 mM Tris/HCl pH 6.8, 8% bromphenolblue). Phosphorylation products were analyzed by SDS-PAGE and auroradiography (x-ray film and phosphor imager).

Example 11
RIP-Kinase Assay

To obtain active RIP kinase the human RIP-cDNA was fused with a DNA sequence coding for the HA-tag and cloned into the eucaryotic expression vector pcDNA3 (Invitrogene). This construct was transfected into human embryonic kidney cells (HEK 293) via the calcium-phosphate DNA co-precipitation method. Two days after transfection cells were washed with PBS and harvested and lysed in lysis-buffer (150 mM NaCl, 1 mM EDTA, 1% Tritron X-100, 20 mM Tris-HCl pH 7.5 and freshly added: 30 mM NaF, 10 µg/ml Aprotinine, 10 µg/ml Leupeptine, 2 mM Na-pyrophosphate). The RIP-HA fusion protein was immunoprecipitated from 250 µl cleared lysate (i.e. lysate of one well of a six-well plate) utilizing an anti-HA antibody from Roche Pharmaceuticals and Protein A sepharose. The sample was rotated for 3 hrs at 4° C. The immunoprecipitates were washed twice with 0.75 ml lysis-buffer, twice with 0.75 ml high salt-buffer (1 M NaCl, 1 mM EDTA, 1% Tritron X-100, 20 mM Tris-HCl pH 7.5 and freshly added: 30 mM NaF, 10 µg/ml Aprotinine, 10 µg/ml Leupeptine, 2 mM Na-pyrophosphate), twice with 0.75 ml lysis-buffer and twice 0.75 ml with kinase assay buffer (10 mM $MgCl_2$, 10 mM $MnCl_2$, 10 mM benzamidine, 0.5 mM EDTA). The kinase reaction was performed directly on the beads in 40 µl kinase assay buffer containing 2.5 µCi $\gamma[^{32}P]$-ATP and various concentrations (between 100 nM and 50 µM) of compounds of Table 2. After 30 min at 30° C., the reaction was stopped by addition of 40 µl 2×Laemmli-buffer. Phosphorylation products were analyzed by SDS-PAGE and autoradiography (x-ray film and phosphor imager).

Example 12
Virus Replication Assay
Cell Culture and Virus

Primary human foreskin fibroblasts (HFF) were cultivated in MEM containing 5% (v/v) fetal calf serum. Infection analysis was restricted to cell passage numbers below twenty. Human cytomegalovirus strain AD169 (ATCC) was grown in HFF cells and quantitated for infectivity by the plaque reduction assay. Aliquots were stored at −80° C.

Construction of Recombinant Cytomegalovirus

For construction of a recombination vector, two linker sequences were inserted into the pBlueScribe vector pBS+ (Stratagene): the first contained restriction sites for NheI, SpeI, PacI and BglII followed by a IoxP sequence (ATAACTTCGTATAGCATACATTATACGAAGTTAT) (SEQ ID NO:6) and was introduced into PstI/XbaI sites of the vector; the second contained another IoxP sequence followed by restriction sites HpaI, ClaI and PmeI and was introduced into BamHI/Asp718 sites. A gene cassette comprising of a "humanized" version of the ORF coding for GEP (gfp-h) under the control of the HCMV enhancer/promoter and the Ptk/PY441 enhancer-driven neoR selection marker was excised from plasmid pUF5 (Zolotukhin et al., 1996, J. Virol. 70, 4646–4654) an inserted into the recombination vector via BglII sites.

At the 5' and 3'-positions of this IoxP-flanked gene cassette, two HCMV sequences with homology to the gene region containing the open reading frames US9 and US10 were inserted. For this, viral sequences were amplified from template pCM49 (Fleckenstein et al., 1989, Gene 18, 39–46) via PCR in a 35-cycle program (denaturation 45 sec at 95° C., annealing 45 sec at 55° C. and elongation 2 mm at 72° C.) by the use of Vent DNA polymerase (New England Biolabs. A US10-specific sequence of 1983 bp in length was generated using primers US10[200900]SpeI (GCTCACTAGTGGCCTAGCCTGGCTCATGGCC) (SEQ ID NO:7) and US10[198918]PacI (GTCCTTAATTAAGACGTGGTTGTGGTCACCGAA) (SEQ ID NO:8 and inserted at the vector 5' cloning position via SpeI/PacI restriction sites (see bold-print). A US9-specific sequence of 2010 bp was generated using primers US9-3'PmeI (CTCGGTTTAAACGACGTGAGGCGCTCCGTCACC) (SEQ ID NO:9) and US-5' ClaI (TTGCATCGATACGGTGTGAGATACCACGATG) (SEQ ID NO:10) inserted at the vector 3' cloning position via PmeI/ClaI restriction sites.

The resulting construct pHM673 was linearized by the use of restriction enzyme NheI and transfected into HEF cells via the electroporation method sing a Gene Pulser (Bio-rad; 280 V, 960 µF, 400 Ω). After 24 h of cultivation, cells were used for infection with 1 PFU/ml of HCMV strain AD169. Selection with 200 µg/ml G418 was started 24 h post infection. Following 3 weeks of passage in the presence of G418, GFP fluorescence could be detected in most of the infected cells. Plaque assays were performed with infectious culture supernatant on HFF cells and single virus plaques were grown by transfer to fresh HFF cells cultured in 48-well plates. DNA was isolated from cells of 32 fluorescence-positive wells and confirmed for the presence of recombinant virus by PCR. For this, primers US9 [1987891] (TGACGCGAGTATTACGTGTC) (SEQ ID NO:11) and US10[199100] (CTCCTCCTGATATGCGGTT) (SEQ ID NO:12) were used resulting in an amplification product of 312 bp for wild-type AD169 virus and approximately 3.5 kb for recombinant virus.

Plaque Assay

HFF cells were cultivated in 12-well plates to 90–100% confluency and used for infection with dilutions of virus-positive cell culture supernatants. Virus inoculation was performed for 90 min at 37° C. under occasional shaking before virus was removed and the cell layers were rinsed with PBS. Overlays of MEM 5% (v/v) fetal calf serum and 0.3% (w/v) agarose were added to each well and all samples were incubated at 37° C. in a 5% $CO_2$ atmosphere for approximately 12 days. Finally, overlays were removed and the formation of foci was visualized by staining with 1% crystal violet in 20% ethanol for 1 min. After repeated rinsing with PBS, plates were air-dried at room temperature and plaque numbers were counted with a light microscope. For the recombinant AD169-GFP virus, quantification of plaque assays could also be performed without crystal violet staining by a direct counting of the amount of green fluorescent plaques using fluorescence microscopy.

Antiviral Compounds

The reference compounds used for antiviral studies, ganciclovir (GCV, Cymeven), foscarnet sodium (FOS, Foscavir) and cidofovir (CDV, Vistide) were purchased from Syntex Arzneimittel (Aachen, Germany), Sigma-Aldrich (Germany) and Pharmacia & Upjohn S. A. (Luxembourg), respectively. Stocks were prepared in aequeous solution and stored at −20° C. The test compounds were dissolved in DMSO and aliquots were stored at −20° C.

GFP infection assay

HFF cells were cultivated in 12-well plates to 90–100% confluency and used for infection with $0.5 \times TCID_{50}$ of AD169-GFP virus. Virus inoculation was performed for 90 min at 37° C. with occasional shaking before virus was removed and the cell layers were rinsed with PBS. Infected cell layers were incubated with 2 ml of MEM containing 5% (v/v) fetal calf serum and optionally of the respective test substances or DMSO as control. Infected cells were incubated at 37° C. in a 5% $CO_2$ atmosphere for 7 days and harvested by trypsination and centrifugation. 200 μl of lysis buffer (25 mM Tris pH 7.8, 2 mM DTT, 2 mM trans-1,2-diaminocyclohexane-N,N,N',N'-tetraacetic acid, 1% Triton X-100, 10% glycerol) was added to each cell pellet and lysis was achieved by incubation for 10 min at 37° C. followed by a 30-min incubation at room temperature on a shaker. Lysates were centrifuged for 5 min at 15.000 rpm in an Eppendorf centrifugue to remove cell debris. Supernatants were transferred to an opaque 96-well plate for automated measuring of GFP signals in a Victor 1420 Multilabel Counter (Wallac). GFP units were converted to percent inhibition values relative to DMSO controls (set at 100% GFP expression).

Indirect Immunofluorescence Analysis

Cells were either grown on Lab-Tek Permanox slides (Nunc) or harvested from 6-well plates, spotted onto glass slides with marked rings (Medco) and fixed by a 15-min treatment with 3% formaldehyde in PBS followed by permeabilization for 15 min in 0.1% Triton X-100 in PBS at room temperature. Blocking was achieved by incubation with Cohn Fraction II/III of human gamma-globulin (Sigma; 2 mg/ml) for 30 min at 37° C. The IE1/IE2-specific primary antibody MAb810 (Chemicon International, Inc. CA, USA; dilution 1:10.000) was incubated for 90 min, the secondary antibody (tetramethyl rhodamine [TRITC]-coupled anti-mouse antibody, Dianova, dilution 1:100) for 45 min at 37° C. before analysis by fluorescence microscopy. In addition to indirect TRITC staining of IE1/IE2 proteins, GFP signals could be detected diretcly via the fluorescence isothiocyanate (FITC) channel. Nuclear counterstaining was carried out using Vectashield mounting medium including DAPI (Vector Laboratories, Burlingame, Calif.).

What is claimed is:

1. Method for identifying compounds useful for treating and/or preventing Cytomegalovirus infection comprising:

a) contacting a test compound with cellular kinase RIP (SEQ ID NO: 16); and b) detecting a decrease in activity of said cellular kinase, wherein said decrease in activity of said cellular kinase indicates said test compound would be useful for treating and/or preventing CMV infection.

* * * * *

SEQUENCE LISTING

```
<160> NUMBER OF SEQ ID NOS: 22

<210> SEQ ID NO 1
<211> LENGTH: 18
<212> TYPE: DNA
<213> ORGANISM: Artificial Sequence
<220> FEATURE:
<223> OTHER INFORMATION: synthetic polyT primer
<220> FEATURE:
<221> NAME/KEY: misc_feature
<222> LOCATION: (18)..(18)
<223> OTHER INFORMATION: n = a,c,g or t
<220> FEATURE:
<221> NAME/KEY: misc_feature
<222> LOCATION: (17)..(17)
<223> OTHER INFORMATION: v = a,g or c

<400> SEQUENCE: 1
tttttttttt tttttttvn                                              18

<210> SEQ ID NO 2
<211> LENGTH: 28
<212> TYPE: DNA
<213> ORGANISM: Artificial Sequence
<220> FEATURE:
<223> OTHER INFORMATION: cDNA probe for NIK-interacting kinase

<400> SEQUENCE: 2
gtcctggagg gctctttttg atgaaacc                                    28

<210> SEQ ID NO 3
<211> LENGTH: 30
<212> TYPE: DNA
<213> ORGANISM: Artificial Sequence
<220> FEATURE:
<223> OTHER INFORMATION: cDNA probe for cellular protein RIP

<400> SEQUENCE: 3
gtgctcaatg cagttgggcc ccttgtacac                                  30

<210> SEQ ID NO 4
<211> LENGTH: 27
<212> TYPE: DNA
<213> ORGANISM: Artificial Sequence
<220> FEATURE:
<223> OTHER INFORMATION: cDNA probe for cellular protein kinase RICK

<400> SEQUENCE: 4
```

```
gtcgagcagc ggagtgtgga tgtgcag                                           27
```

<210> SEQ ID NO 5
<211> LENGTH: 23
<212> TYPE: PRT
<213> ORGANISM: Artificial Sequence
<220> FEATURE:
<223> OTHER INFORMATION: NIK peptide immunogen

<400> SEQUENCE: 5

Cys Asn Pro Thr Asn Thr Arg Pro Gln Ser Asp Thr Pro Glu Ile Arg
1               5                   10                  15

Lys Tyr Lys Lys Arg Phe Asn
            20

<210> SEQ ID NO 6
<211> LENGTH: 34
<212> TYPE: DNA
<213> ORGANISM: Artificial Sequence
<220> FEATURE:
<223> OTHER INFORMATION: loxP sequence for recombination vector

<400> SEQUENCE: 6

```
ataacttcgt atagcataca ttatacgaag ttat                                   34
```

<210> SEQ ID NO 7
<211> LENGTH: 31
<212> TYPE: DNA
<213> ORGANISM: Artificial Sequence
<220> FEATURE:
<223> OTHER INFORMATION: primer US-10(200900)SpeI

<400> SEQUENCE: 7

```
gctcactagt ggcctagcct ggctcatggc c                                      31
```

<210> SEQ ID NO 8
<211> LENGTH: 33
<212> TYPE: DNA
<213> ORGANISM: Artificial Sequence
<220> FEATURE:
<223> OTHER INFORMATION: primer US-10(198918)PacI

<400> SEQUENCE: 8

```
gtccttaatt aagacgtggt tgtggtcacc gaa                                    33
```

<210> SEQ ID NO 9
<211> LENGTH: 33
<212> TYPE: DNA
<213> ORGANISM: Artificial Sequence
<220> FEATURE:
<223> OTHER INFORMATION: primer US-9-3'PmeI

<400> SEQUENCE: 9

```
ctcggtttaa acgacgtgag gcgctccgtc acc                                    33
```

<210> SEQ ID NO 10
<211> LENGTH: 31
<212> TYPE: DNA
<213> ORGANISM: Artificial Sequence
<220> FEATURE:
<223> OTHER INFORMATION: primer US-5'ClAI

<400> SEQUENCE: 10

```
ttgcatcgat acggtgtgag ataccacgat g                                      31
```

<210> SEQ ID NO 11
<211> LENGTH: 20
<212> TYPE: DNA
<213> ORGANISM: Artificial Sequence
<220> FEATURE:
<223> OTHER INFORMATION: primer US-9(198789)

<400> SEQUENCE: 11

| tgacgcgagt attacgtgtc | 20 |
|---|---|

<210> SEQ ID NO 12
<211> LENGTH: 19
<212> TYPE: DNA
<213> ORGANISM: Artificial Sequence
<220> FEATURE:
<223> OTHER INFORMATION: primer US-10(199100)

<400> SEQUENCE: 12

| ctcctcctga tatgcggtt | 19 |
|---|---|

<210> SEQ ID NO 13
<211> LENGTH: 2501
<212> TYPE: DNA
<213> ORGANISM: Homo sapiens

<400> SEQUENCE: 13

| ggcaccagtc tctagaaaag aagtcagctc tggttcggag aagcagcggc tggcgtgggc | 60 |
|---|---|
| catccgggga tgggcgccc tcgtgaccta gtgttgcggg gcaaaaaggg tcttgccggc | 120 |
| ctcgctcgtg caggggcgta tctgggcgcc tgagcgcgca gtgggagcct gggagccgc | 180 |
| cgcagcaggg ggcacacccg gaaccggcct gagcgcccgg gaccatgaac ggggaggcca | 240 |
| tctgcagcgc cctgcccacc attccctacc acaaactcgc cgacctgcgc tacctgagcc | 300 |
| gcggcgcctc tggcactgtg tcgtccgccc gccacgcaga ctggcgcgtc caggtggccg | 360 |
| tgaagcacct gcacatccac actccgctgc tcgacagtga agaaaggat gtcttaagag | 420 |
| aagctgaaat tttacacaaa gctagattta gttacattct tccaattttg ggaatttgca | 480 |
| atgagcctga ttttggga atagttactg aatacatgcc aaatggatca ttaaatgaac | 540 |
| tcctacatag gaaaactgaa tatcctgatg ttgcttggcc attgagattt cgcatcctgc | 600 |
| atgaaattgc cctggtgta aattacctgc acaatatgac tcctccttta cttcatcatg | 660 |
| acttgaagac tcagaatatc ttattggaca atgaatttca tgttaagatt gcagattttg | 720 |
| gtttatcaaa gtggcgcatg atgtccctct cacagtcacg aagtagcaaa tctgcaccag | 780 |
| aaggagggac aattatctat atgccacctg aaaactatga acctggacaa aaatcaaggg | 840 |
| ccagtatcaa gcacgatata tatagctatg cagttatcac atgggaagtg ttatccagaa | 900 |
| aacagccttt tgaagatgtc accaatcctt tgcagataat gtatagtgtg tcacaaggac | 960 |
| atcgacctgt tattaatgaa gaaagtttgc catatgatat acctcaccga gcacgtatga | 1020 |
| tctctctaat agaaagtgga tgggcacaaa atccagatga agaccatct ttcttaaaat | 1080 |
| gtttaataga acttgaacca gttttgagaa catttgaaga gataactttt cttgaagctg | 1140 |
| ttattcagct aaagaaaaca aagttacaga gtgtttcaag tgccattcac ctatgtgaca | 1200 |
| agaagaaaat ggaattatct ctgaacatac ctgtaaatca tggtccacaa gaggaatcat | 1260 |
| gtggatcctc tcagctccat gaaaatagtg gttctcctga aacttcaagg tccctgccag | 1320 |
| ctcctcaaga caatgatttt ttatctagaa aagctcaaga ctgttattt atgaagctgc | 1380 |
| atcactgtcc tggaaatcac agttgggata gcaccatttc tggttctcaa agggctgcat | 1440 |

-continued

```
tctgtgatca caagaccact ccatgctctt cagcaataat aaatccactc tcaactgcag    1500
gaaactcaga acgtctgcag cctggtatag cccagcagtg gatccagagc aaaagggaag    1560
acattgtgaa ccaaatgaca gaagcctgcc ttaaccagtc gctagatgcc cttctgtcca    1620
gggacttgat catgaaagag gactatgaac ttgttagtac caagcctaca aggacctcaa    1680
aagtcagaca attactagac actactgaca tccaaggaga agaatttgcc aaagttatag    1740
tacaaaaatt gaaagataac aaacaaatgg gtcttcagcc ttacccggaa atacttgtgg    1800
tttctagatc accatctttta aatttacttc aaaataaaag catgtaagtg actgtttttc    1860
aagaagaaat gtgtttcata aaggatatt tatatctctg ttgctttgac ttttttttata    1920 taaaatccgt gagtattaaa gctttattga aggttctttg ggtaaatatt agtctccctc    1980
catgacactg cagtatttttt tttaattaat acaagtaaaa agttgaattt ggttgaattt    2040
gctacatagt tcaatttttta tgtctctttt gttaacagaa accactttta aaggatagta    2100
attattcttg tttataacag tgccttaagg tatgatgtat ttctgatgga agccattttc    2160
acattcatgt tcttcatgga ttatttgtta cttgtctaag atgcaatttg attttatgaa    2220
gtatataccc tttacccacc agagacagta cagaatccct gccctaaaat cccaggctta    2280
attgccctac aaagggttat taatttaaaa ctccattatt aggattacat tttaaagttt    2340
tatttatgaa ttccctttaa aaatgatatt tcaaaggtaa aacaatacaa tataaagaaa    2400
aaaataaata tattaatacc ggcttcctgt ccccattttt aacctcagcc ttccctactg    2460
tcaccaacaa ccaagctaaa taaagtcaac agcctgatgt g                       2501
```

<210> SEQ ID NO 14
<211> LENGTH: 540
<212> TYPE: PRT
<213> ORGANISM: Homo sapiens

<400> SEQUENCE: 14

```
Met Asn Gly Glu Ala Ile Cys Ser Ala Leu Pro Thr Ile Pro Tyr His
1               5                   10                  15

Lys Leu Ala Asp Leu Arg Tyr Leu Ser Arg Gly Ala Ser Gly Thr Val
            20                  25                  30

Ser Ser Ala Arg His Ala Asp Trp Arg Val Gln Val Ala Val Lys His
        35                  40                  45

Leu His Ile His Thr Pro Leu Leu Asp Ser Glu Arg Lys Asp Val Leu
    50                  55                  60

Arg Glu Ala Glu Ile Leu His Lys Ala Arg Phe Ser Tyr Ile Leu Pro
65                  70                  75                  80

Ile Leu Gly Ile Cys Asn Glu Pro Glu Phe Leu Gly Ile Val Thr Glu
                85                  90                  95

Tyr Met Pro Asn Gly Ser Leu Asn Glu Leu Leu His Arg Lys Thr Glu
            100                 105                 110

Tyr Pro Asp Val Ala Trp Pro Leu Arg Phe Arg Ile Leu His Glu Ile
        115                 120                 125

Ala Leu Gly Val Asn Tyr Leu His Asn Met Thr Pro Pro Leu Leu His
    130                 135                 140

His Asp Leu Lys Thr Gln Asn Ile Leu Leu Asp Asn Glu Phe His Val
145                 150                 155                 160

Lys Ile Ala Asp Phe Gly Leu Ser Lys Trp Arg Met Met Ser Leu Ser
                165                 170                 175

Gln Ser Arg Ser Ser Lys Ser Ala Pro Glu Gly Gly Thr Ile Ile Tyr
            180                 185                 190
```

-continued

```
Met Pro Pro Glu Asn Tyr Glu Pro Gly Gln Lys Ser Arg Ala Ser Ile
            195                 200                 205
Lys His Asp Ile Tyr Ser Tyr Ala Val Ile Thr Trp Glu Val Leu Ser
    210                 215                 220
Arg Lys Gln Pro Phe Glu Asp Val Thr Asn Pro Leu Gln Ile Met Tyr
225                 230                 235                 240
Ser Val Ser Gln Gly His Arg Pro Val Ile Asn Glu Glu Ser Leu Pro
                245                 250                 255
Tyr Asp Ile Pro His Arg Ala Arg Met Ile Ser Leu Ile Glu Ser Gly
            260                 265                 270
Trp Ala Gln Asn Pro Asp Glu Arg Pro Ser Phe Leu Lys Cys Leu Ile
        275                 280                 285
Glu Leu Glu Pro Val Leu Arg Thr Phe Glu Glu Ile Thr Phe Leu Glu
    290                 295                 300
Ala Val Ile Gln Leu Lys Lys Thr Lys Leu Gln Ser Val Ser Ser Ala
305                 310                 315                 320
Ile His Leu Cys Asp Lys Lys Met Glu Leu Ser Leu Asn Ile Pro
                325                 330                 335
Val Asn His Gly Pro Gln Glu Glu Ser Cys Gly Ser Ser Gln Leu His
            340                 345                 350
Glu Asn Ser Gly Ser Pro Glu Thr Ser Arg Ser Leu Pro Ala Pro Gln
        355                 360                 365
Asp Asn Asp Phe Leu Ser Arg Lys Ala Gln Asp Cys Tyr Phe Met Lys
    370                 375                 380
Leu His His Cys Pro Gly Asn His Ser Trp Asp Ser Thr Ile Ser Gly
385                 390                 395                 400
Ser Gln Arg Ala Ala Phe Cys Asp His Lys Thr Thr Pro Cys Ser Ser
                405                 410                 415
Ala Ile Ile Asn Pro Leu Ser Thr Ala Gly Asn Ser Glu Arg Leu Gln
            420                 425                 430
Pro Gly Ile Ala Gln Gln Trp Ile Gln Ser Lys Arg Glu Asp Ile Val
        435                 440                 445
Asn Gln Met Thr Glu Ala Cys Leu Asn Gln Ser Leu Asp Ala Leu Leu
    450                 455                 460
Ser Arg Asp Leu Ile Met Lys Glu Asp Tyr Glu Leu Val Ser Thr Lys
465                 470                 475                 480
Pro Thr Arg Thr Ser Lys Val Arg Gln Leu Leu Asp Thr Thr Asp Ile
                485                 490                 495
Gln Gly Glu Glu Phe Ala Lys Val Ile Val Gln Lys Leu Lys Asp Asn
            500                 505                 510
Lys Gln Met Gly Leu Gln Pro Tyr Pro Glu Ile Leu Val Val Ser Arg
        515                 520                 525
Ser Pro Ser Leu Asn Leu Leu Gln Asn Lys Ser Met
    530                 535                 540

<210> SEQ ID NO 15
<211> LENGTH: 2617
<212> TYPE: DNA
<213> ORGANISM: Homo sapiens
<220> FEATURE:
<221> NAME/KEY: misc_feature
<222> LOCATION: (2141)..(2141)
<223> OTHER INFORMATION: n = a,c,g or t
<220> FEATURE:
<221> NAME/KEY: misc_feature
<222> LOCATION: (2311)..(2311)
```

-continued

```
<223> OTHER INFORMATION: n = a,c,g or t
<220> FEATURE:
<221> NAME/KEY: misc_feature
<222> LOCATION: (2452)..(2452)
<223> OTHER INFORMATION: n = a,c,g or t
<220> FEATURE:
<221> NAME/KEY: misc_feature
<222> LOCATION: (2496)..(2496)
<223> OTHER INFORMATION: n = a,c,g or t

<400> SEQUENCE: 15
atgcaaccag acatgtcctt gaatgtcatt aagatgaaat ccagtgactt cctggagagt      60
gcagaactgg acagcggagg ctttgggaag gtgtctctgt gtttccacag aacccaggga     120
ctcatgatca tgaaaacagt gtacaagggg cccaactgca ttgagcacaa cgaggccctc     180
ttggaggagg cgaagatgat gaacagactg agacacagcc gggtggtgaa gctcctgggc     240
gtcatcatag aggaagggaa gtactccctg tgatggagt acatggagaa gggcaacctg     300
atgcacgtgc tgaaagccga gatgagtact ccgctttctg taaaaggaag gataattttg     360
gaaatcattg aaggaatgtg ctacttacat ggaaaggcg tgatacacaa ggacctgaag     420
cctgaaaata tccttgttga taatgacttc cacattaaga tcgcagacct cggccttgcc     480
tcctttaaga tgtggagcaa actgaataat gaagagcaca atgagctgag ggaagtggac     540
ggcaccgcta agaagaatgg cggcacccte tactacatgg cgcccgagca cctgaatgac     600
gtcaacgcaa agcccacaga gaagtcggat gtgtacagct ttgctgtagt actctgggcg     660
atatttgcaa ataaggagcc atatgaaaat gctatctgtg agcagcagtt gataatgtgc     720
ataaaatctg gaacaggcc agatgtggat gacatcactg agtactgccc aagagaaatt     780
atcagtctca tgaagctctg ctgggaagcg aatccggaag ctcggccgac atttcctggc     840
attgaagaaa aatttaggcc ttttttattta agtcaattag aagaaagtgt agaagaggac     900
gtgaagagtt taagaaaga gtattcaaac gaaaatgcag ttgtgaagag aatgcagtct     960
cttcaacttg attgtgtggc agtaccttca agccggtcaa attcagccac agaacagcct    1020
ggttcactgc acagttccca gggacttggg atgggtcctg tggaggagtc ctggtttgct    1080
ccttccctgg agcacccaca agaagagaat gagcccagcc tgcagagtaa actccaagac    1140
gaagccaact accatcttta tggcagccgc atggacaggc agacgaaaca gcagcccaga    1200
cagaatgtgg cttacaacag agaggaggaa aggagacgca gggtctccca tgacccttt     1260 gcacagcaaa gaccttacga gaatttcag aatacagagg gaaaaggcac tgtttattcc    1320
agtgcagcca gtcatggtaa tgcagtgcac cagccctcag ggctcaccag ccaacctcaa    1380
gtactgtatc agaacaatgg attatatagc tcacatggct ttggaacaag accactggat    1440
ccaggaacag caggtcccag agtttggtac aggccaattc caagtcatat gcctagtctg    1500
cataatatcc cagtgcctga gaccaactat ctaggaaata cacccaccat gccattcagc    1560
tccttgccac caacagatga atctataaaa tataccatat acaatagtac tggcattcag    1620
attggagcct acaattatat ggagattggt ggacgagtt catcactact agacagcaca    1680
aatacgaact tcaaagaaga gccagctgct aagtaccaag ctatctttga taataccact    1740
agtctgacgg ataaacacct ggacccaatc agggaaaatc tgggaaagca ctggaaaaac    1800
tgtgcccgta aactgggctt cacacagtct cagattgatg aaattgacca tgactatgag    1860
cgagatggac tgaaagaaaa ggtttaccag atgctccaaa agtgggtgat gagggaaggc    1920
ataaagggag ccacggtggg gaagctggcc caggcgctcc accagtgttc caggatcgac    1980
cttctgagca gcttgattta cgtcagccag aactaaccct ggatgggcta cggcagctga    2040
```

-continued

```
agtggacgcc tcacttagcg ataaccccca gaaagttggc tgcctcagag cattcagaat    2100
tctgtcctca ctgatagggg ttctgtgtct gcagaaattt ngtttcctgt acttcatagc    2160
tggagaatgg ggaaagaaat ctgcagcaaa ggggtctcac tctgttgcca ggctggtctc    2220
aaacttctgg actcaagtga tcctcccgcc tcggccttcc aaagtgctgg gatatcaggc    2280
actgagccac tgcgcccagt caacaatccg ntctgaggaa agcgtaagca ggaagacctc    2340
ttaatggcat agcaccaata aaaaaatgac tcctagttgt gtttggaaag ggagagaaga    2400
gatgtctgag gaaggtcatg ttctttcagc ttatggcatt tcctagagtt tngttgaagc    2460
aagaagaaaa actcagagaa tataaaatca actttnaaaa ttgtgtgctc tcttcttcac    2520
gtaggctcct gttaaaaaca aagtgcagtc agattctaag ccctgttcag agacttcgcg    2580
gatcacagct gcagctcacc gccacatcac aggatcc                             2617
```

<210> SEQ ID NO 16
<211> LENGTH: 671
<212> TYPE: PRT
<213> ORGANISM: Homo sapiens

<400> SEQUENCE: 16

```
Met Gln Pro Asp Met Ser Leu Asn Val Ile Lys Met Lys Ser Ser Asp
1               5                   10                  15

Phe Leu Glu Ser Ala Glu Leu Asp Ser Gly Gly Phe Gly Lys Val Ser
            20                  25                  30

Leu Cys Phe His Arg Thr Gln Gly Leu Met Ile Met Lys Thr Val Tyr
        35                  40                  45

Lys Gly Pro Asn Cys Ile Glu His Asn Glu Ala Leu Leu Glu Glu Ala
    50                  55                  60

Lys Met Met Asn Arg Leu Arg His Ser Arg Val Val Lys Leu Leu Gly
65                  70                  75                  80

Val Ile Ile Glu Glu Gly Lys Tyr Ser Leu Val Met Glu Tyr Met Glu
                85                  90                  95

Lys Gly Asn Leu Met His Val Leu Lys Ala Glu Met Ser Thr Pro Leu
            100                 105                 110

Ser Val Lys Gly Arg Ile Ile Leu Glu Ile Ile Glu Gly Met Cys Tyr
        115                 120                 125

Leu His Gly Lys Gly Val Ile His Lys Asp Leu Lys Pro Glu Asn Ile
    130                 135                 140

Leu Val Asp Asn Asp Phe His Ile Lys Ile Ala Asp Leu Gly Leu Ala
145                 150                 155                 160

Ser Phe Lys Met Trp Ser Lys Leu Asn Asn Glu Glu His Asn Glu Leu
                165                 170                 175

Arg Glu Val Asp Gly Thr Ala Lys Lys Asn Gly Gly Thr Leu Tyr Tyr
            180                 185                 190

Met Ala Pro Glu His Leu Asn Asp Val Asn Ala Lys Pro Thr Glu Lys
        195                 200                 205

Ser Asp Val Tyr Ser Phe Ala Val Val Leu Trp Ala Ile Phe Ala Asn
    210                 215                 220

Lys Glu Pro Tyr Glu Asn Ala Ile Cys Glu Gln Gln Leu Ile Met Cys
225                 230                 235                 240

Ile Lys Ser Gly Asn Arg Pro Asp Val Asp Asp Ile Thr Glu Tyr Cys
                245                 250                 255

Pro Arg Glu Ile Ile Ser Leu Met Lys Leu Cys Trp Glu Ala Asn Pro
            260                 265                 270
```

-continued

```
Glu Ala Arg Pro Thr Phe Pro Gly Ile Glu Glu Lys Phe Arg Pro Phe
            275                 280                 285
Tyr Leu Ser Gln Leu Glu Glu Ser Val Glu Glu Asp Val Lys Ser Leu
        290                 295                 300
Lys Lys Glu Tyr Ser Asn Glu Asn Ala Val Val Lys Arg Met Gln Ser
305                 310                 315                 320
Leu Gln Leu Asp Cys Val Ala Val Pro Ser Ser Arg Ser Asn Ser Ala
                    325                 330                 335
Thr Glu Gln Pro Gly Ser Leu His Ser Ser Gln Gly Leu Gly Met Gly
            340                 345                 350
Pro Val Glu Glu Ser Trp Phe Ala Pro Ser Leu Glu His Pro Gln Glu
        355                 360                 365
Glu Asn Glu Pro Ser Leu Gln Ser Lys Leu Gln Asp Glu Ala Asn Tyr
    370                 375                 380
His Leu Tyr Gly Ser Arg Met Asp Arg Gln Thr Lys Gln Gln Pro Arg
385                 390                 395                 400
Gln Asn Val Ala Tyr Asn Arg Glu Glu Glu Arg Arg Arg Arg Val Ser
                    405                 410                 415
His Asp Pro Phe Ala Gln Arg Pro Tyr Glu Asn Phe Gln Asn Thr
            420                 425                 430
Glu Gly Lys Gly Thr Val Tyr Ser Ser Ala Ser His Gly Asn Ala
        435                 440                 445
Val His Gln Pro Ser Gly Leu Thr Ser Gln Pro Gln Val Leu Tyr Gln
    450                 455                 460
Asn Asn Gly Leu Tyr Ser Ser His Gly Phe Gly Thr Arg Pro Leu Asp
465                 470                 475                 480
Pro Gly Thr Ala Gly Pro Arg Val Trp Tyr Arg Pro Ile Pro Ser His
                    485                 490                 495
Met Pro Ser Leu His Asn Ile Pro Val Pro Glu Thr Asn Tyr Leu Gly
            500                 505                 510
Asn Thr Pro Thr Met Pro Phe Ser Ser Leu Pro Pro Thr Asp Glu Ser
        515                 520                 525
Ile Lys Tyr Thr Ile Tyr Asn Ser Thr Gly Ile Gln Ile Gly Ala Tyr
    530                 535                 540
Asn Tyr Met Glu Ile Gly Gly Thr Ser Ser Leu Leu Asp Ser Thr
545                 550                 555                 560
Asn Thr Asn Phe Lys Glu Glu Pro Ala Ala Lys Tyr Gln Ala Ile Phe
                    565                 570                 575
Asp Asn Thr Thr Ser Leu Thr Asp Lys His Leu Asp Pro Ile Arg Glu
            580                 585                 590
Asn Leu Gly Lys His Trp Lys Asn Cys Ala Arg Lys Leu Gly Phe Thr
        595                 600                 605
Gln Ser Gln Ile Asp Glu Ile Asp His Asp Tyr Glu Arg Asp Gly Leu
    610                 615                 620
Lys Glu Lys Val Tyr Gln Met Leu Gln Lys Trp Val Met Arg Glu Gly
625                 630                 635                 640
Ile Lys Gly Ala Thr Val Gly Lys Leu Ala Gln Ala Leu His Gln Cys
                    645                 650                 655
Ser Arg Ile Asp Leu Leu Ser Ser Leu Ile Tyr Val Ser Gln Asn
            660                 665                 670

<210> SEQ ID NO 17
<211> LENGTH: 4596
```

<212> TYPE: DNA
<213> ORGANISM: Homo sapiens

<400> SEQUENCE: 17

| | | | | | |
|---|---|---|---|---|---|
| aagcggggga | ctgtgccgtg | tggaacgtgt | agctgttgag | aggtggactc | tgttaccatt | 60 |
| gaggatgttt | ggaggatgag | tatgtgtggc | agaggcacac | ataaacaggc | agagaccctt | 120 |
| tgcccctgcc | tttctccccc | aacccaaggc | tgacctgtgt | tctcccaggt | ctgggattct | 180 |
| aagtgacctg | ctctgtgttt | ggtctctctc | aggatgagca | caagcctggg | agatggcagt | 240 |
| gatggaaatg | gcctgcccag | gtgcccctgg | ctcagcagtg | gggcagcaga | aggaactccc | 300 |
| caagccaaag | gagaagacgc | cgccactggg | gaagaaacag | agctccgtct | acaagcttga | 360 |
| ggccgtggag | aagagccctg | tgttctgcgg | aaagtgggag | atcctgaatg | acgtgattac | 420 |
| caagggcaca | gccaaggaag | gctccgaggc | agggccagct | gccatctcta | tcatcgccca | 480 |
| ggctgagtgt | gagaatagcc | aagagttcag | ccccaccttt | tcagaacgca | ttttcatcgc | 540 |
| tgggtccaaa | cagtacagcc | agtccgagag | tcttgatcag | atccccaaca | atgtggccca | 600 |
| tgctacagag | ggcaaaatgg | cccgtgtgtg | ttggaaggga | aagcgtcgca | gcaaagcccg | 660 |
| gaagaaacgg | aagaagaaga | gctcaaagtc | cctggctcat | gcaggagtgg | ccttggccaa | 720 |
| acccctcccc | aggaccccctg | agcaggagag | ctgcaccatc | ccagtgcagg | aggatgagtc | 780 |
| tccactcggc | gccccatatg | ttagaaacac | cccgcagttc | accaagcctc | tgaaggaacc | 840 |
| aggccttggg | caactctgtt | ttaagcagct | tggcgagggc | ctacggccgg | ctctgcctcg | 900 |
| atcagaactc | cacaaactga | tcagcccctt | gcaatgtctg | aaccacgtgt | ggaaactgca | 960 |
| ccaccccag | gacggaggcc | cctgccccct | gcccacgcac | cccttcccct | atagcagact | 1020 |
| gcctcatccc | ttcccattcc | accctctcca | gccctggaaa | cctcaccctc | tggagtcctt | 1080 |
| cctgggcaaa | ctggcctgtg | tagacagcca | gaaaccttg | cctgacccac | acctgagcaa | 1140 |
| actggcctgt | gtagacagtc | caaagcccct | gcctggccca | cacctggagc | ccagctgcct | 1200 |
| gtctcgtggt | gcccatgaga | agttttctgt | ggaggaatac | ctagtgcatg | ctctgcaagg | 1260 |
| cagcgtgagc | tcaagccagg | cccacagcct | gaccagcctg | gccaagacct | gggcagcacg | 1320 |
| gggctccaga | tcccgggagc | ccagccccaa | aactgaggac | aacgagggtg | tcctgctcac | 1380 |
| tgagaaactc | aagccagtgg | attatgagta | ccgagaagaa | gtccactggg | ccacgcacca | 1440 |
| gctccgcctg | ggcagaggct | ccttcggaga | ggtgcacagg | atggaggaca | gcagactgg | 1500 |
| cttccagtgc | gctgtcaaaa | aggtgcggct | ggaagtattt | cggcagagg | agctgatggc | 1560 |
| atgtgcagga | ttgacctcac | ccagaattgt | ccctttgtat | ggagctgtga | gagaagggcc | 1620 |
| ttgggtcaac | atcttcatgg | agctgctgga | aggtggctcc | ctgggccagc | tggtcaagga | 1680 |
| gcagggctgt | ctcccagagg | accgggccct | gtactacctg | gccaggccc | tggagggtct | 1740 |
| ggaatacctc | cactcacgaa | ggattctgca | tgggacgtc | aaagctgaca | acgtgctcct | 1800 |
| gtccagcgat | gggagccacg | cagccctctg | tgactttggc | catgctgtgt | gtcttcaacc | 1860 |
| tgatggcctg | ggaaagtcct | tgctcacagg | ggactacatc | cctggcacag | agacccacat | 1920 |
| ggctccggag | gtggtgctgg | gcaggagctg | cgacgccaag | gtggatgtct | ggagcagctg | 1980 |
| ctgtatgatg | ctgcacatgc | tcaacggctg | ccaccctgg | actcagttct | tccgagggcc | 2040 |
| gctctgcctc | aagattgcca | gcgagcctcc | gcctgtgagg | gagatcccac | cctcctgcgc | 2100 |
| ccctctcaca | gcccaggcca | tccaagaggg | gctgaggaaa | gagcccatcc | accgcgtgtc | 2160 |
| tgcagcggag | ctgggaggga | aggtgaaccg | ggcactacag | caagtgggag | gtctgaagag | 2220 |

| | |
|---|---|
| cccttggagg ggagaatata aagaaccaag acatccaccg ccaaatcaag ccaattacca | 2280 |
| ccagaccctc catgcccagc cgagagagct ttcgccaagg gccccagggc cccggccagc | 2340 |
| tgaggagaca acaggcagag cccctaagct ccagcctcct ctcccaccag agccccagga | 2400 |
| gccaaacaag tctcctccct tgactttgag caaggaggag tctgggatgt gggaacccct | 2460 |
| acctctgtcc tccctggagc cagcccctgc cagaaacccc agctcaccag agcggaaagc | 2520 |
| aaccgtcccg gagcaggaac tgcagcagct ggaaatagaa ttattcctca acagcctgtc | 2580 |
| ccagccattt tctctggagg agcaggagca aattctctcg tgcctcagca tcgacagcct | 2640 |
| ctccctgtcg gatgacagtg agaagaaccc atcaaaggcc tctcaaagct cgcgggacac | 2700 |
| cctgagctca ggcgtacact cctggagcag ccaggccgag gctcgaagct ccagctggaa | 2760 |
| catggtgctg gcccgggggc ggcccaccga cacccccaagc tatttcaatg gtgtgaaagt | 2820 |
| ccaaatacag tctcttaatg gtgaacacct gcacatccgg gagttccacc gggtcaaagt | 2880 |
| gggagacatc gccactggca tcagcagcca gatcccagct gcagccttca gcttggtcac | 2940 |
| caaagacggg cagcctgttc gctacgacat ggaggtgcca gactcgggca tcgacctgca | 3000 |
| gtgcacactg gcccctgatg gcagcttcgc ctggagctgg agggtcaagc atggccagct | 3060 |
| ggagaacagg ccctaacccct gccctccacc gccggctcca cactgccgga aagcagcctt | 3120 |
| cctgctcggt gcacgatgct gccctgaaaa cacaggctca gccgttccca ggggattgcc | 3180 |
| agccccccgg ctcacagtgg gaaccagggc ctcgcagcag caaggtgggg gcaagcagaa | 3240 |
| tgcctcccag gatttcacac ctgagccctg ccccaccctg ctgaaaaaac atccgccacg | 3300 |
| tgaagagaca gaaggaggat ggcaggagtt acctggggaa acaaaacagg gatcttttc | 3360 |
| tgcccctgct ccagtcgagt tggcctgacc cgcttggatc agtgaccatt tgttggcaga | 3420 |
| caggggagag cagcttccag cctgggtcag aagggggtggg cgagcccttc ggcccctcac | 3480 |
| cctccaggct gctgtgagag tgtcaagtgt gtaagggccc aaactcaggt tcagtgcaga | 3540 |
| accaggtcag caggtatgcc cgcccgtagg ttaaggggc cctctaaacc ccttgcctgg | 3600 |
| cctcacctgg ccagctcacc ccttttgggt gtaggggaaa agaatgcctg acctggggaa | 3660 |
| ggctccctgg tagaatacac cacacttttc aggttgttgc aacacaggtc ctgagttgac | 3720 |
| ctctggttca gccaaggacc aaagaaggtg tgtaagtgaa gtggttctca gtccccagac | 3780 |
| atgtgcccct ttgctgctgg ctaccactct tccccagagc agcaggcccc gagccccttc | 3840 |
| aggcccagca ctgccccaga ctcgctggca ctcagttccc tcatctgtaa aggtgaaggg | 3900 |
| tgatgcagga tatgcctgac aggaacagtc tgtggatgga catgatcagt gctaaggaaa | 3960 |
| gcagcagaga gagacgtccg gcgcccccagc cccactatca gtgtccagcg tgctggttcc | 4020 |
| ccagagcaca gctcagcatc acactgacac tcaccctgcc ctgcccctgg ccagagggta | 4080 |
| ctgccgacgg cactttgcac tctgatgacc tcaaagcact ttcatggctg ccctctggca | 4140 |
| gggcagggca gggcagtgac actgtaggag catagcaagc caggagatgg ggtgaaggga | 4200 |
| cacagtcttg agctgtccac atgcatgtga ctcctcaaac ctcttccaga tttctctaag | 4260 |
| aatagcaccc ccttcccccat tgccccagct tagcctcttc tcccaggga gctactcagg | 4320 |
| actcacgtag cattaaatca gctgtgaatc gtcaggggt gtctgctagc ctcaacctcc | 4380 |
| tggggcaggg gacgccgaga ctccgtggga gaagctcatt cccacatctt gccaagacag | 4440 |
| cctttgtcca gctgtccaca ttgagtcaga ctgctcccgg ggagagagcc ccggccccca | 4500 |
| gcacataaag aactgcagcc ttggtactgc agagtctggg ttgtagagaa ctctttgtaa | 4560 |
| gcaataaagt ttggggtgat gacaaatgtt aaaaaa | 4596 |

<210> SEQ ID NO 18
<211> LENGTH: 947
<212> TYPE: PRT
<213> ORGANISM: Homo sapiens

<400> SEQUENCE: 18

```
Met Ala Val Met Glu Met Ala Cys Pro Gly Ala Pro Gly Ser Ala Val
1               5                   10                  15

Gly Gln Gln Lys Glu Leu Pro Lys Pro Lys Glu Lys Thr Pro Pro Leu
            20                  25                  30

Gly Lys Lys Gln Ser Ser Val Tyr Lys Leu Glu Ala Val Glu Lys Ser
        35                  40                  45

Pro Val Phe Cys Gly Lys Trp Glu Ile Leu Asn Asp Val Ile Thr Lys
    50                  55                  60

Gly Thr Ala Lys Glu Gly Ser Glu Ala Gly Pro Ala Ala Ile Ser Ile
65                  70                  75                  80

Ile Ala Gln Ala Glu Cys Glu Asn Ser Gln Glu Phe Ser Pro Thr Phe
                85                  90                  95

Ser Glu Arg Ile Phe Ile Ala Gly Ser Lys Gln Tyr Ser Gln Ser Glu
            100                 105                 110

Ser Leu Asp Gln Ile Pro Asn Asn Val Ala His Ala Thr Glu Gly Lys
        115                 120                 125

Met Ala Arg Val Cys Trp Lys Gly Lys Arg Arg Ser Lys Ala Arg Lys
    130                 135                 140

Lys Arg Lys Lys Lys Ser Ser Lys Ser Leu Ala His Ala Gly Val Ala
145                 150                 155                 160

Leu Ala Lys Pro Leu Pro Arg Thr Pro Glu Gln Glu Ser Cys Thr Ile
                165                 170                 175

Pro Val Gln Glu Asp Glu Ser Pro Leu Gly Ala Pro Tyr Val Arg Asn
            180                 185                 190

Thr Pro Gln Phe Thr Lys Pro Leu Lys Glu Pro Gly Leu Gly Gln Leu
        195                 200                 205

Cys Phe Lys Gln Leu Gly Glu Gly Leu Arg Pro Ala Leu Pro Arg Ser
    210                 215                 220

Glu Leu His Lys Leu Ile Ser Pro Leu Gln Cys Leu Asn His Val Trp
225                 230                 235                 240

Lys Leu His His Pro Gln Asp Gly Gly Pro Leu Pro Leu Pro Thr His
                245                 250                 255

Pro Phe Pro Tyr Ser Arg Leu Pro His Pro Phe Pro Phe His Pro Leu
            260                 265                 270

Gln Pro Trp Lys Pro His Pro Leu Glu Ser Phe Leu Gly Lys Leu Ala
        275                 280                 285

Cys Val Asp Ser Gln Lys Pro Leu Pro Asp Pro His Leu Ser Lys Leu
    290                 295                 300

Ala Cys Val Asp Ser Pro Lys Pro Leu Pro Gly Pro His Leu Glu Pro
305                 310                 315                 320

Ser Cys Leu Ser Arg Gly Ala His Glu Lys Phe Ser Val Glu Glu Tyr
                325                 330                 335

Leu Val His Ala Leu Gln Gly Ser Val Ser Ser Gln Ala His Ser
            340                 345                 350

Leu Thr Ser Leu Ala Lys Thr Trp Ala Ala Arg Gly Ser Arg Ser Arg
        355                 360                 365

Glu Pro Ser Pro Lys Thr Glu Asp Asn Glu Gly Val Leu Leu Thr Glu
```

-continued

```
            370                 375                 380
Lys Leu Lys Pro Val Asp Tyr Glu Tyr Arg Glu Val His Trp Ala
385                 390                 395                 400

Thr His Gln Leu Arg Leu Gly Arg Gly Ser Phe Gly Glu Val His Arg
                405                 410                 415

Met Glu Asp Lys Gln Thr Gly Phe Gln Cys Ala Val Lys Lys Val Arg
                420                 425                 430

Leu Glu Val Phe Arg Ala Glu Glu Leu Met Ala Cys Ala Gly Leu Thr
                435                 440                 445

Ser Pro Arg Ile Val Pro Leu Tyr Gly Ala Val Arg Glu Gly Pro Trp
450                 455                 460

Val Asn Ile Phe Met Glu Leu Leu Glu Gly Gly Ser Leu Gly Gln Leu
465                 470                 475                 480

Val Lys Glu Gln Gly Cys Leu Pro Glu Asp Arg Ala Leu Tyr Tyr Leu
                485                 490                 495

Gly Gln Ala Leu Glu Gly Leu Glu Tyr Leu His Ser Arg Arg Ile Leu
                500                 505                 510

His Gly Asp Val Lys Ala Asp Asn Val Leu Leu Ser Ser Asp Gly Ser
                515                 520                 525

His Ala Ala Leu Cys Asp Phe Gly His Ala Val Cys Leu Gln Pro Asp
                530                 535                 540

Gly Leu Gly Lys Ser Leu Leu Thr Gly Asp Tyr Ile Pro Gly Thr Glu
545                 550                 555                 560

Thr His Met Ala Pro Glu Val Val Leu Gly Arg Ser Cys Asp Ala Lys
                565                 570                 575

Val Asp Val Trp Ser Ser Cys Cys Met Met Leu His Met Leu Asn Gly
                580                 585                 590

Cys His Pro Trp Thr Gln Phe Phe Arg Gly Pro Leu Cys Leu Lys Ile
                595                 600                 605

Ala Ser Glu Pro Pro Val Arg Glu Ile Pro Pro Ser Cys Ala Pro
610                 615                 620

Leu Thr Ala Gln Ala Ile Gln Glu Gly Leu Arg Lys Glu Pro Ile His
625                 630                 635                 640

Arg Val Ser Ala Ala Glu Leu Gly Gly Lys Val Asn Arg Ala Leu Gln
                645                 650                 655

Gln Val Gly Gly Leu Lys Ser Pro Trp Arg Gly Glu Tyr Lys Glu Pro
                660                 665                 670

Arg His Pro Pro Asn Gln Ala Asn Tyr His Gln Thr Leu His Ala
                675                 680                 685

Gln Pro Arg Glu Leu Ser Pro Arg Ala Pro Gly Pro Arg Pro Ala Glu
                690                 695                 700

Glu Thr Thr Gly Arg Ala Pro Lys Leu Gln Pro Pro Leu Pro Pro Glu
705                 710                 715                 720

Pro Pro Glu Pro Asn Lys Ser Pro Pro Leu Thr Leu Ser Lys Glu Glu
                725                 730                 735

Ser Gly Met Trp Glu Pro Leu Pro Leu Ser Ser Leu Glu Pro Ala Pro
                740                 745                 750

Ala Arg Asn Pro Ser Ser Pro Glu Arg Lys Ala Thr Val Pro Glu Gln
                755                 760                 765

Glu Leu Gln Gln Leu Glu Ile Glu Leu Phe Leu Asn Ser Leu Ser Gln
                770                 775                 780

Pro Phe Ser Leu Glu Glu Gln Glu Gln Ile Leu Ser Cys Leu Ser Ile
785                 790                 795                 800
```

```
Asp Ser Leu Ser Leu Ser Asp Asp Ser Glu Lys Asn Pro Ser Lys Ala
                805                 810                 815

Ser Gln Ser Ser Arg Asp Thr Leu Ser Ser Gly Val His Ser Trp Ser
            820                 825                 830

Ser Gln Ala Glu Ala Arg Ser Ser Ser Trp Asn Met Val Leu Ala Arg
        835                 840                 845

Gly Arg Pro Thr Asp Thr Pro Ser Tyr Phe Asn Gly Val Lys Val Gln
    850                 855                 860

Ile Gln Ser Leu Asn Gly Glu His Leu His Ile Arg Glu Phe His Arg
865                 870                 875                 880

Val Lys Val Gly Asp Ile Ala Thr Gly Ile Ser Ser Gln Ile Pro Ala
                885                 890                 895

Ala Ala Phe Ser Leu Val Thr Lys Asp Gly Gln Pro Val Arg Tyr Asp
                900                 905                 910

Met Glu Val Pro Asp Ser Gly Ile Asp Leu Gln Cys Thr Leu Ala Pro
            915                 920                 925

Asp Gly Ser Phe Ala Trp Ser Trp Arg Val Lys His Gly Gln Leu Glu
    930                 935                 940

Asn Arg Pro
945

<210> SEQ ID NO 19
<211> LENGTH: 2030
<212> TYPE: DNA
<213> ORGANISM: Homo sapiens

<400> SEQUENCE: 19
tggctggcaa tggccttgct gacctcgagc cgggcccacg tggggacctt tggagcacag    60
cctacgatcc tggtgcaagg ccggtggatg cagaggccag tccatatacc acccaggcct   120
gcgaggagcg tggtccccac ccatccagcc catatgtgca agtgcccttg acagagaggc   180
tggtcatatc catggtgacc atttatgggc acaacaggt ccccatctgc gcagtgaacc    240
ctgtgctgag caccttgcag acgtgatctt gcttcgtcct gcagcactgt gcggggcagg   300
aaaatccaag aggaagaagg atctacggat atcctgcatg tccaagccac ccgcacccaa   360
ccccacaccc ccccggaacc tggactcccg gaccttcatc accattggag acagaaactt   420
tgaggtggag gctgatgact tggtgaccat ctcagaactg gccgtggag cctatggggt    480
ggtagagaag gtgcggcacg cccagagcgg caccatcatg gccgtgaagc ggatccgggc   540
caccgtgaac tcacaggagc agaagcggct gctcatggac ctggacatca acatgcgcac   600
ggtcgactgt ttctacactg tcaccttcta cggggcacta ttcagagagg agacgtgtg    660
gatctgcatg gagctcatgg acacatcctt ggacaagttc taccggaagg tgctggataa   720
aaacatgaca attccagagg acatccttgg ggagattgct gtgtctatcg tgcgggccct   780
ggagcatctg cacagcaagc tgtcggtgat ccacagagat gtgaagccct ccaatgtcct   840
tatcaacaag gagggccatg tgaagatgtg tgactttggc atcagtggct acttggtgga   900
ctctgtggcc aagacgatgg atgccggctg caagccctac atggcccctg agaggatcaa   960
cccagagctg aaccagaagg gctacaatgt caagtccgac gtctggagcc tgggcatcac  1020
catgattgag atggccatcc tgcggttccc ttacgagtcc tggggaccc cgttccagca  1080
gctgaagcag gtggtggagg agccgtcccc ccagctccca gccgaccgtt ctccccccga  1140
gtttgtggac ttcactgctc agtgcctgag gaagaacccc gcagagcgta tgagctacct  1200
```

```
ggagctgatg gagcacccct tcttcacctt gcacaaaacc aagaagacgg acattgctgc   1260
cttcgtgaag aagatcctgg gagaagactc ataggggctg ggcctcggac cccactccgg   1320
ccctccagag ccccacagcc ccatctgcgg gggcagtgct cacccacacc ataagctact   1380
gccatcctgg cccagggcat ctgggaggaa ccgaggggc tgctcccacc tggctctgtg    1440
gcgagccatt tgtcccaagt gccaagaag cagaccattg ggctcccag ccaggccctt     1500 gtcggcccca ccagtgcctc tccctgctgc tcctaggacc cgtctccagc tgctgagatc   1560
ctggactgag ggggcctgga tgccccctgt ggatgctgct gccctgcac agcaggctgc    1620 cagtgcctgg gtggatgggc caccgccttg cccagcctgg atgccatcca agttgtatat   1680
ttttttaatc tctcgactga atggactttg cacactttgg cccagggtgg ccacacctct   1740
atcccggctt tggtgcgggg tacacaagag gggatgagtt gtgtgaatac cccaagactc   1800
ccatgaggga gatgccatga gccgcccaag gccttcccct ggcactggca aacagggcct   1860
ctgcggagca cactggctca cccagtcctg cccgccaccg ttatcggtgt cattcacctt   1920
tcgtgttttt tttaatttat cctctgttga ttttttcttt tgctttatgg gtttggcttg   1980 ttttcttgc atggtttgga gctgatcgct tctcccccac cccctagggg              2030
```

<210> SEQ ID NO 20
<211> LENGTH: 318
<212> TYPE: PRT
<213> ORGANISM: Homo sapiens

<400> SEQUENCE: 20

```
Met Ser Lys Pro Pro Ala Pro Asn Pro Thr Pro Pro Arg Asn Leu Asp
1               5                   10                  15

Ser Arg Thr Phe Ile Thr Ile Gly Asp Arg Asn Phe Glu Val Glu Ala
            20                  25                  30

Asp Asp Leu Val Thr Ile Ser Glu Leu Gly Arg Gly Ala Tyr Gly Val
        35                  40                  45

Val Glu Lys Val Arg His Ala Gln Ser Gly Thr Ile Met Ala Val Lys
    50                  55                  60

Arg Ile Arg Ala Thr Val Asn Ser Gln Glu Gln Lys Arg Leu Leu Met
65                  70                  75                  80

Asp Leu Asp Ile Asn Met Arg Thr Val Asp Cys Phe Tyr Thr Val Thr
                85                  90                  95

Phe Tyr Gly Ala Leu Phe Arg Glu Gly Asp Val Trp Ile Cys Met Glu
            100                 105                 110

Leu Met Asp Thr Ser Leu Asp Lys Phe Tyr Arg Lys Val Leu Asp Lys
        115                 120                 125

Asn Met Thr Ile Pro Glu Asp Ile Leu Gly Glu Ile Ala Val Ser Ile
    130                 135                 140

Val Arg Ala Leu Glu His Leu His Ser Lys Leu Ser Val Ile His Arg
145                 150                 155                 160

Asp Val Lys Pro Ser Asn Val Leu Ile Asn Lys Glu Gly His Val Lys
                165                 170                 175

Met Cys Asp Phe Gly Ile Ser Gly Tyr Leu Val Asp Ser Val Ala Lys
            180                 185                 190

Thr Met Asp Ala Gly Cys Lys Pro Tyr Met Ala Pro Glu Arg Ile Asn
        195                 200                 205

Pro Glu Leu Asn Gln Lys Gly Tyr Asn Val Lys Ser Asp Val Trp Ser
    210                 215                 220

Leu Gly Ile Thr Met Ile Glu Met Ala Ile Leu Arg Phe Pro Tyr Glu
```

```
                225                 230                 235                 240
Ser Trp Gly Thr Pro Phe Gln Gln Leu Lys Gln Val Val Glu Glu Pro
                    245                 250                 255
Ser Pro Gln Leu Pro Ala Asp Arg Phe Ser Pro Glu Phe Val Asp Phe
            260                 265                 270
Thr Ala Gln Cys Leu Arg Lys Asn Pro Ala Glu Arg Met Ser Tyr Leu
        275                 280                 285
Glu Leu Met Glu His Pro Phe Phe Thr Leu His Lys Thr Lys Lys Thr
    290                 295                 300
Asp Ile Ala Ala Phe Val Lys Lys Ile Leu Gly Glu Asp Ser
305                 310                 315

<210> SEQ ID NO 21
<211> LENGTH: 3745
<212> TYPE: DNA
<213> ORGANISM: Homo sapiens

<400> SEQUENCE: 21
```

| | | | | | |
|---|---|---|---|---|---|
| gaattcggca | cgaggccatt | gaatcccagt | cctaacagaa | gtactgcgaa | tcttgtggcc | 60 |
| tcattctgaa | caaaagggat | tagagaagaa | aaatctcttg | atataaggct | tgaaagcaag | 120 |
| ggcaggcaat | cttggttgtg | aatattttct | gattttccca | gaaatcaagc | agaagattga | 180 |
| gctgctgatg | tcagttaact | ctgagaagtc | gtcctcttca | gaaaggccgg | agcctcaaca | 240 |
| gaaagctcct | ttagttcctc | ctcctccacc | gccaccacca | ccaccaccgc | cacctttgcc | 300 |
| agaccccaca | cccccggagc | cagaggagga | gatcctggga | tcagatgatg | aggagcaaga | 360 |
| ggaccctgcg | gactactgca | aggtggata | tcatccagtg | aaaattggag | acctcttcaa | 420 |
| tggccggtat | catgttatta | gaaagcttgg | atggggcac | ttctctactg | tctggctgtg | 480 |
| ctgggatatg | caggggaaaa | gatttgttgc | aatgaaagtt | gtaaaagtg | cccagcatta | 540 |
| tacgagaca | gccttggatg | aaataaaatt | gctcaaatgt | gttcgagaaa | gtgatcccag | 600 |
| tgacccaaac | aaagacatgg | tggtccagct | cattgacgac | ttcaagattt | caggcatgaa | 660 |
| tgggatacat | gtctgcatgg | tcttcgaagt | acttggccac | catctcctca | agtggatcat | 720 |
| caaatccaac | tatcaaggcc | tcccagtacg | ttgtgtgaag | agtatcattc | gacaggtcct | 780 |
| tcaagggtta | gattacttac | acagtaagtg | caagatcatt | catactgaca | taagccgga | 840 |
| aaatatcttg | atgtgtgtgg | atgatgcata | tgtgagaaga | atggcagctg | agcctgagtg | 900 |
| gcagaaagca | ggtgctcctc | ctccttcagg | gtctgcagtg | agtacggctc | acagcagaa | 960 |
| acctatagga | aaaatatcta | aaacaaaaa | gaaaaactg | aaaagaaac | agaagaggca | 1020 |
| ggctgagtta | ttggagaagc | gcctgcagga | gatagaagaa | ttggagcgag | aagctgaaag | 1080 |
| gaaaataata | gaagaaaaca | tcacctcagc | tgcaccttcc | aatgaccagg | atggcgaata | 1140 |
| ctgcccagag | gtgaaactaa | aacaacagg | attagaggag | gcggctgagg | cagagactgc | 1200 |
| aaaggacaat | ggtgaagctg | aggaccagga | agagaaagaa | gatgctgaga | aagaaaacat | 1260 |
| tgaaaaagat | gaagatgatg | tagatcagga | acttgcgaac | atagacccta | cgtggataga | 1320 |
| atcacctaaa | accaatggcc | atattgagaa | tggcccattc | tcactggagc | agcaactgga | 1380 |
| cgatgaagat | gatgatgaag | aagactgccc | aaatcctgag | gaatataatc | ttgatgagcc | 1440 |
| aaatgcagaa | agtgattaca | catatagcag | ctcctatgaa | caattcaatg | gtgaattgcc | 1500 |
| aaatggacga | cataaaaattc | ccgagtcaca | gttcccagag | ttttccacct | cgttgttctc | 1560 |
| tggatcctta | gaacctgtgg | cctgcggctc | tgtgctttct | gagggatcac | cacttactga | 1620 |

-continued

| | | | |
|---|---|---|---|
| gcaagaggag agcagtccat cccatgacag aagcagaacg gtttcagcct ccagtactgg | | | 1680 |
| ggatttgcca aaagcaaaaa cccgggcagc tgacttgttg gtgaatcccc tggatccgcg | | | 1740 |
| gaatcgagat aaaattagag taaaaattgc tgacctggga aatgcttgtt gggtgcataa | | | 1800 |
| acacttcacg gaagacatcc agacgcgtca gtaccgctcc atagaggttt taataggagc | | | 1860 |
| ggggtacagc accctgcgg acatctggag cacggcgtgt atggcatttg agctggcaac | | | 1920 |
| gggagattat ttgtttgaac cacattctgg ggaagactat tccagagacg aagaccacat | | | 1980 |
| agcccacatc atagagctgc taggcagtat tccaaggcac tttgctctat ctggaaaata | | | 2040 |
| ttctcgggaa ttcttcaatc gcagaggaga actgcgacac atcaccaagc tgaagccctg | | | 2100 |
| gagcctcttt gatgtacttg tggaaaagta tggctggccc catgaagatg ctgcacagtt | | | 2160 |
| tacagatttc ctgatcccga tgttagaaat ggttccagaa aaacgagcct cagctggcga | | | 2220 |
| atgtcggcat ccttggttga attcttagca aattctacca atattgcatt ctgagctagc | | | 2280 |
| aaatgttccc agtacattgg acctaaacgt gactctcat tctttaacag gattacaagt | | | 2340 |
| gagctggctt catcctcaga cctttatttt gctttgaggt actgttgttt gacattttgc | | | 2400 |
| tttttgtgca ctgtgatcct ggggaagggt agtcttttgt cttcagctaa gtagtttact | | | 2460 |
| gaccattttc ttctggaaac aataacatgt ctctaagcat tgtttcttgt gttgtgtgac | | | 2520 |
| attcaaatgt cattttttg aatgaaaaat acttccccct ttgtgttttg gcaggttttg | | | 2580 |
| taactattta tgaagaaata ttttagctga gtactatata atttacaatc ttaagaaatt | | | 2640 |
| atcaagttgg aaccaagaaa tagcaaggaa atgtacaatt ttatcttctg gcaaaggggac | | | 2700 |
| atcattcctg tattatagtg tatgtaaatg caccctgtaa atgttacttt ccattaaata | | | 2760 |
| tgggaggggg actcaaattt cagaaaagct accaagtctt gagtgctttg tagcctatgt | | | 2820 |
| tgcatgtagc ggactttaac tgctccaagg agttgtgcaa acttttcatt ccataacagt | | | 2880 |
| cttttcacat tggattttaa acaaagtggc tctgggttat aagatgtcat tctctatatg | | | 2940 |
| gcactttaaa ggaagaaaag atatgttctt cattctaaaa tatgcattat aatttagcag | | | 3000 |
| tcccatttgt gattttgcat attttttaaaa gtacttttaa agaagagcaa tttcccttta | | | 3060 |
| aaaatgtgat ggctcagtac catgtcatgt tgcctcctct gggcgctgta agttaagctc | | | 3120 |
| tacatagatt aaaattggaga aacgtgttaa ttgtgtggaa tgaaaaaata catatatttt | | | 3180 |
| tggaaaagca tgatcatgct tgtctagaac acaaggtatg gtatatacaa tttgcagtgc | | | 3240 |
| agtgggcaga atacttctca cagctcaaag ataacagtga tcacattcat tccataggta | | | 3300 |
| gctttacgtg tggctacaac aaattttact agcttttttca ttgtcttttcc atgaaacgaa | | | 3360 |
| gttgagaaaa tgattttccc tttgcaggtt gcacacagtt ttgtttatgc atttccttaa | | | 3420 |
| aattaattgt agactccagg atacaaacca tagtaggcaa tacaatttag aatgtaatat | | | 3480 |
| atagaggtat attagcctct ttagaagtca gtggattgaa tgtcttttta ttttaaattt | | | 3540 |
| tacattcatt aaggtgcctc gttttgact ttgtccatta acatttatcc atatgccttt | | | 3600 |
| gcaataacta gattgtgaaa agctaacaag tgttgtaaca ataatccatt gtttgaggtg | | | 3660 |
| cttgcagttg tcttaaaaat taaagtgttt tggttttttt ttttccagaa aaaaaaaaa | | | 3720 |
| aaaaaaaaa aaaaaaatt cctgc | | | 3745 |

<210> SEQ ID NO 22
<211> LENGTH: 686
<212> TYPE: PRT
<213> ORGANISM: Homo sapiens

<400> SEQUENCE: 22

```
Met Ser Val Asn Ser Glu Lys Ser Ser Ser Glu Arg Pro Glu Pro
1               5                   10                  15

Gln Gln Lys Ala Pro Leu Val Pro Pro Pro Pro Pro Pro Pro Pro
            20              25                  30

Pro Pro Pro Pro Leu Pro Asp Pro Thr Pro Pro Glu Pro Glu Glu Glu
        35              40                  45

Ile Leu Gly Ser Asp Asp Glu Gln Glu Asp Pro Ala Asp Tyr Cys
    50                  55                  60

Lys Gly Gly Tyr His Pro Val Lys Ile Gly Asp Leu Phe Asn Gly Arg
65                  70                  75                  80

Tyr His Val Ile Arg Lys Leu Gly Trp Gly His Phe Ser Thr Val Trp
                85                  90                  95

Leu Cys Trp Asp Met Gln Gly Lys Arg Phe Val Ala Met Lys Val Val
                100                 105                 110

Lys Ser Ala Gln His Tyr Thr Glu Thr Ala Leu Asp Glu Ile Lys Leu
            115                 120                 125

Leu Lys Cys Val Arg Glu Ser Asp Pro Ser Asp Pro Asn Lys Asp Met
130                 135                 140

Val Val Gln Leu Ile Asp Asp Phe Lys Ile Ser Gly Met Asn Gly Ile
145                 150                 155                 160

His Val Cys Met Val Phe Glu Val Leu Gly His His Leu Leu Lys Trp
                165                 170                 175

Ile Ile Lys Ser Asn Tyr Gln Gly Leu Pro Val Arg Cys Val Lys Ser
                180                 185                 190

Ile Ile Arg Gln Val Leu Gln Gly Leu Asp Tyr Leu His Ser Lys Cys
            195                 200                 205

Lys Ile Ile His Thr Asp Ile Lys Pro Glu Asn Ile Leu Met Cys Val
210                 215                 220

Asp Asp Ala Tyr Val Arg Arg Met Ala Ala Glu Pro Glu Trp Gln Lys
225                 230                 235                 240

Ala Gly Ala Pro Pro Pro Ser Gly Ser Ala Val Ser Thr Ala Pro Gln
                245                 250                 255

Gln Lys Pro Ile Gly Lys Ile Ser Lys Asn Lys Lys Lys Leu Lys
            260                 265                 270

Lys Lys Gln Lys Arg Gln Ala Glu Leu Leu Glu Lys Arg Leu Gln Glu
            275                 280                 285

Ile Glu Glu Leu Glu Arg Glu Ala Glu Arg Lys Ile Ile Glu Glu Asn
290                 295                 300

Ile Thr Ser Ala Ala Pro Ser Asn Asp Gln Asp Gly Glu Tyr Cys Pro
305                 310                 315                 320

Glu Val Lys Leu Lys Thr Thr Gly Leu Glu Glu Ala Ala Glu Ala Glu
            325                 330                 335

Thr Ala Lys Asp Asn Gly Glu Ala Glu Asp Gln Glu Glu Lys Glu Asp
            340                 345                 350

Ala Glu Lys Glu Asn Ile Glu Lys Asp Glu Asp Val Asp Gln Glu
            355                 360                 365

Leu Ala Asn Ile Asp Pro Thr Trp Ile Glu Ser Pro Lys Thr Asn Gly
370                 375                 380

His Ile Glu Asn Gly Pro Phe Ser Leu Glu Gln Leu Asp Asp Glu
385                 390                 395                 400

Asp Asp Asp Glu Glu Asp Cys Pro Asn Pro Glu Glu Tyr Asn Leu Asp
                405                 410                 415
```

-continued

```
Glu Pro Asn Ala Glu Ser Asp Tyr Thr Tyr Ser Ser Ser Tyr Glu Gln
            420                 425                 430

Phe Asn Gly Glu Leu Pro Asn Gly Arg His Lys Ile Pro Glu Ser Gln
        435                 440                 445

Phe Pro Glu Phe Ser Thr Ser Leu Phe Ser Gly Ser Leu Glu Pro Val
    450                 455                 460

Ala Cys Gly Ser Val Leu Ser Glu Gly Ser Pro Leu Thr Glu Gln Glu
465                 470                 475                 480

Glu Ser Ser Pro Ser His Asp Arg Ser Arg Thr Val Ser Ala Ser Ser
                485                 490                 495

Thr Gly Asp Leu Pro Lys Ala Lys Thr Arg Ala Ala Asp Leu Leu Val
            500                 505                 510

Asn Pro Leu Asp Pro Arg Asn Arg Asp Lys Ile Arg Val Lys Ile Ala
            515                 520                 525

Asp Leu Gly Asn Ala Cys Trp Val His Lys His Phe Thr Glu Asp Ile
    530                 535                 540

Gln Thr Arg Gln Tyr Arg Ser Ile Glu Val Leu Ile Gly Ala Gly Tyr
545                 550                 555                 560

Ser Thr Pro Ala Asp Ile Trp Ser Thr Ala Cys Met Ala Phe Glu Leu
                565                 570                 575

Ala Thr Gly Asp Tyr Leu Phe Glu Pro His Ser Gly Glu Asp Tyr Ser
            580                 585                 590

Arg Asp Glu Asp His Ile Ala His Ile Ile Glu Leu Leu Gly Ser Ile
                595                 600                 605

Pro Arg His Phe Ala Leu Ser Gly Lys Tyr Ser Arg Glu Phe Phe Asn
    610                 615                 620

Arg Arg Gly Glu Leu Arg His Ile Thr Lys Leu Lys Pro Trp Ser Leu
625                 630                 635                 640

Phe Asp Val Leu Val Glu Lys Tyr Gly Trp Pro His Glu Asp Ala Ala
                645                 650                 655

Gln Phe Thr Asp Phe Leu Ile Pro Met Leu Glu Met Val Pro Glu Lys
            660                 665                 670

Arg Ala Ser Ala Gly Glu Cys Arg His Pro Trp Leu Asn Ser
            675                 680                 685
```